United States Patent
Chen et al.

(10) Patent No.: US 11,860,170 B2
(45) Date of Patent: Jan. 2, 2024

(54) ASSAY METHOD FOR THE DETECTION OF VCAM-1 AND ALPHA-2-MACROGLOBULIN IN BLOOD

(71) Applicant: PROCISEDX INC., San Diego, CA (US)

(72) Inventors: Hongyu Chen, San Diego, CA (US); Limin Liu, San Diego, CA (US); Stefan Westin, San Diego, CA (US); Michael Hale, San Diego, CA (US); Larry Mimms, San Diego, CA (US)

(73) Assignee: ProciseDX Inc., San Diego, CA (US)

( * ) Notice: Subject to any disclaimer, the term of this patent is extended or adjusted under 35 U.S.C. 154(b) by 0 days.

(21) Appl. No.: 17/508,619

(22) Filed: Oct. 22, 2021

(65) Prior Publication Data

US 2023/0139053 A1 May 4, 2023

Related U.S. Application Data

(63) Continuation of application No. PCT/US2020/032973, filed on May 14, 2020.

(60) Provisional application No. 62/848,713, filed on May 16, 2019.

(51) Int. Cl.
*G01N 33/53* (2006.01)
*G01N 33/68* (2006.01)
*G01N 21/64* (2006.01)
G01N 33/542 (2006.01)

(52) U.S. Cl.
CPC ..... *G01N 33/6893* (2013.01); *G01N 21/6408* (2013.01); *G01N 21/6428* (2013.01); *G01N 33/542* (2013.01); *G01N 2021/6439* (2013.01); *G01N 2333/4713* (2013.01); *G01N 2333/70542* (2013.01); *G01N 2800/085* (2013.01)

(58) Field of Classification Search
CPC .. G01N 33/53; G01N 33/6893; G01N 33/542; G01N 21/6408; G01N 21/6428; G01N 2021/6439; G01N 2333/4713; G01N 2333/70542; G01N 2800/085
See application file for complete search history.

(56) References Cited

U.S. PATENT DOCUMENTS

| | | | | |
|---|---|---|---|---|
| 5,158,869 A | * | 10/1992 | Pouletty | G01N 33/54366 |
| | | | | 435/973 |
| 5,968,765 A | * | 10/1999 | Grage | G01N 33/52 |
| | | | | 435/14 |
| 2005/0170442 A1 | * | 8/2005 | Kupcho | C12Q 1/42 |
| | | | | 435/15 |
| 2013/0203068 A1 | * | 8/2013 | Roby | G01N 21/6428 |
| | | | | 435/7.1 |
| 2013/0345073 A1 | | 12/2013 | Seguin et al. | |
| 2016/0349251 A1 | * | 12/2016 | Hao | G01N 33/533 |
| 2017/0219611 A1 | * | 8/2017 | Ward | G01N 33/6896 |
| 2017/0370925 A1 | * | 12/2017 | Sheehan | G01N 33/558 |
| 2021/0405063 A1 | | 12/2021 | Liu et al. | |

FOREIGN PATENT DOCUMENTS

| | | |
|---|---|---|
| EP | 3821250 B1 | 4/2017 |
| WO | 2020236528 A1 | 11/2020 |
| WO | 2020247159 A1 | 12/2020 |
| WO | 2020263450 A1 | 12/2020 |

OTHER PUBLICATIONS

Jeyakumar e al., A dual-acceptor time-resolved foster resonance energy transfer assay for simultaneous determination of thyroid hormone regulation of corepressor and coactivator binding to the thyroid hormone receptor, Anal Biochem, Mar. 1, 2009, 386(1), pp. 1-14 (Year: 2009).*
Kupcho et al., Simultaneous monitoring of discrete binding events using dual-acceptor terbium-based LRET, J. Am. Chem. Soc, 2007, 129, pp. 13372-13373. (Year: 2007).*
Degorce et al., HTRF: A Technology Tailored for Drug Discovery—A Review of Theoretical Aspects and Recent Applications, Current Chemical Genomics, vol. 3, Available Online at: https://www.ncbi.nlm.nih.gov/pmc/articles/PMC2802762/pdf/TOCHGENJ-3-22.pdf, Jan. 1, 2009, pp. 22-32.
Geibler et al., Six-Color Time-Resolved Forster Resonance Energy Transfer for Ultrasensitive Multiplexed Biosensing, Journal of The American Chemical Society, vol. 135, Issue 3, Jan. 23, 2013, pp. 1102-1109.
Ghale-Noie et al., High Serum Alpha-2-Macroglobulin Level in Patients with Osteonecrosis of the Femoral Head, Available Online at: https://www.ncbi.nlm.nih.gov/pmc/articles/PMC5990713/pdf/ABJS-6-219.pdf, vol. 6, Issue 3, Jan. 1, 2018, pp. 219-224.
Horton et al., Multiplexing Terbium- and Europium-Based TR-FRET Readouts to Increase Kinase Assay Capacity, Journal of Biomolecular Screening, vol. 15, Issue 8, May 10, 2010, pp. 1008-1015.
Patel et al., Multiplex Protein Analysis to Determine Fibrosis Stage and Progression in Patients with Chronic Hepatitis C, Clinical Gastroenterology and Hepatology, vol. 12, Issue 12, Dec. 1, 2014, 11 pages.
International Application No. PCT/US2020/032973, International Search Report and Written Opinion dated Aug. 18, 2020, 15 pages.
Tas et al., Serum Levels of Vascular Cell Adhesion Molecule-1 (VCAM-1) may have Diagnostic, Predictive, and Prognostic Roles in Patients with Lung Cancer Treated with Platinum-Based Chemotherapy, Tumor Biology, vol. 35, Issue 8, May 15, 2014, pp. 7871-7875.

(Continued)

*Primary Examiner* — Gary Counts
(74) *Attorney, Agent, or Firm* — KILPATRICK TOWNSEND & STOCKTON LLP

(57) ABSTRACT

An assay method for detecting the presence or amounts of VCAM-1 and A2M in a sample using fluorescence resonance energy transfer (FRET).

20 Claims, 9 Drawing Sheets

Specification includes a Sequence Listing.

(56) References Cited

OTHER PUBLICATIONS

Young, Cytokine Multiplex Analysis, Methods in Molecular Biology, vol. 511, 2009, 29 pages.

* cited by examiner 026-11B

Alexa647-NHS

Alexa647

ASSAY METHOD FOR THE DETECTION OF VCAM-1 AND ALPHA-2-MACROGLOBULIN IN BLOOD

CROSS-REFERENCES TO RELATED APPLICATIONS

This application is a continuation of PCT/US2020/032973, filed May 14, 2020, which application claims priority to U.S. Provisional Application No. 62/848,713, filed May 16, 2019, the disclosures of which are hereby incorporated by reference in their entireties for all purposes.

BACKGROUND OF THE INVENTION

Some biological assays rely on time-resolved fluorescence resonance energy transfer (TR-FRET) mechanisms where two fluorophores are used. Biological materials are typically prone to autofluorescence, which can be minimized by utilizing time-resolved FRET. TR-FRET takes advantage of rare earth elements such as lanthanides (e.g., europium and terbium), which have exceptionally long fluorescence emission half-lives. In these assays, energy is transferred between a donor fluorophore and an acceptor fluorophore if the two fluorophore are in close proximity to one another. Excitation of the donor (e.g., cryptate) by an energy source (e.g., UV light) produces an energy transfer to the acceptor, if the two fluorophores are within a given proximity. In turn, the acceptor emits light at its characteristic wavelength. In order for TR-FRET to occur, the fluorescence emission spectrum of the donor molecule must overlap with the absorption or excitation spectrum of the acceptor chromophore. Moreover, the fluorescence lifetime of the donor molecule must be of sufficient duration to allow TR-FRET to occur.

Cryptates can be used in various bioassays formats. Cryptates are complexes that include a macrocycle within which a lanthanide ion such as terbium or europium is tightly embedded or chelated. This cage like structure is useful for collecting irradiated energy and transferring the collected energy to the lanthanide ion. The lanthanide ion can release the energy with a characteristic fluorescence.

U.S. Pat. No. 6,406,297 is titled "Salicylamide-lanthanide complexes for use as luminescent markers." This patent is directed to luminescent lanthanide metal chelates comprising a metal ion of the lanthanide series and a complexing agent comprising a salicylamidyl moiety. This patent is hereby incorporated by reference.

U.S. Pat. No. 6,515,113 is titled "Phthalamide lanthanide complexes for use as luminescent markers." This patent is directed to luminescent lanthanide metal chelates comprising a metal ion of the lanthanide series and a complexing agent comprising a phthalamidyl moiety. This patent is hereby incorporated by reference.

WO2015157057 is titled "Macrocycles" and relates to chemical compounds and complexes that can be used in therapeutic and diagnostic applications. This publication contains cryptate molecules useful for labeling biomolecules. This publication is hereby incorporated by reference.

WO2018130988 discloses cryptates derivatives and conjugates thereof with excellent fluorescent properties. The cryptates are useful in biological assays and methods for the detection and identification of various analytes.

Vascular cell adhesion protein 1, also known as vascular cell adhesion molecule 1 (VCAM-1) or cluster of differentiation 106 (CD106), is a protein that in humans is encoded by the VCAM-1 gene. VCAM-1 functions as a cell adhesion molecule. Alpha-2-Macroglobulin (A2M) is a large (approximately 720 kDa) plasma protein found in the blood. A2M mainly acts as an antiprotease and is able to inactivate a variety of proteinases. For example, it functions as an inhibitor of fibrinolysis by inhibiting plasmin and kallikrein. It functions as an inhibitor of coagulation by inhibiting thrombin. Further, A2M sometimes acts as a carrier protein because it also binds to numerous growth factors and cytokines, such as platelet-derived growth factor, basic fibroblast growth factor, TGF-β, insulin, and IL-1β. The presence and concentration levels of VCAM-1 or A2M are typically measured by an enzyme-linked immunosorbent assay (ELISA).

VCAM-1 or A2M solid-phase sandwich ELISA is designed to measure the presence or amount of the analyte bound between an antibody pair. In the sandwich ELISA, a sample is added to an immobilized capture antibody. After a second (detector) antibody is added, a substrate solution is used that reacts with an enzyme-antibody-target complex to produce a measurable signal. The intensity of this signal is proportional to the concentration of target present in the test sample In view of the foregoing, what is needed in the art is a homogeneous assay that can measure the presence or amount of VCAM-1 and A2M simultaneously to provide an increase in flexibility, reliability, and sensitivity in addition to higher throughput. The present disclosure provides this and other needs.

BRIEF SUMMARY

In one aspect, the present disclosure provides an assay method for detecting the presence or amount of VCAM-1 and A2M in a sample, the method comprising:

contacting the sample with a first anti-VCAM-1 antibody, which binds to a first epitope of VCAM-1, wherein the first anti-VCAM-1 antibody is labeled with a first donor fluorophore;

contacting the sample with a second anti-VCAM-1 antibody, which binds to a second epitope of VCAM-1, wherein the second anti-VCAM-1 antibody is labeled with a first acceptor fluorophore;

contacting the sample with an anti-A2M antibody, which binds to an epitope of A2M, wherein the anti-A2M antibody is labeled with a second donor fluorophore;

contacting the sample with an isolated A2M protein, wherein the isolated A2M protein is labeled with a second acceptor fluorophore;

incubating the sample for a time sufficient to obtain dual labeled VCAM-1 and labeled A2M; and exciting the sample having dual labeled VCAM-1 and labeled A2M using one or more light sources to detect at least one fluorescence emission signal associated with fluorescence resonance energy transfer (FRET), wherein the first and second acceptor fluorophores are different.

In another aspect, the present disclosure provides an assay method for detecting the presence or amount of VCAM-1 and A2M in a sample, the method comprising:

contacting the sample with a first anti-VCAM-1 antibody having a first binding epitope to VCAM-1, wherein the first anti-VCAM-1 antibody is labeled with a first donor fluorophore;

contacting the sample with a second anti-VCAM-1 antibody, which binds to a second epitope of VCAM-1, wherein the second anti-VCAM-1 antibody is labeled with a first acceptor fluorophore;

contacting the sample with an anti-A2M antibody, which binds to an epitope of A2M, wherein the anti-A2M antibody is labeled with a second acceptor fluorophore;

contacting the sample with an isolated A2M protein, wherein the isolated A2M protein is labeled with a second donor fluorophore;

incubating the sample for a time sufficient to obtain dual labeled VCAM-1 and labeled A2M; and exciting the sample having dual labeled VCAM-1 and labeled A2M using one or more light sources to detect at least one fluorescence emission signal associated with fluorescence resonance energy transfer (FRET), wherein the first and second acceptor fluorophores are different.

In some embodiments of the second aspect of the disclosure, the first and second donor fluorophores are the same and the sample is excited using one light source. In other embodiments, the first and second donor fluorophores are different and the sample is excited using two different light sources.

In some embodiments, the FRET emission signals are time resolved FRET emission signals.

In some embodiments, the sample is a biological sample (e.g., whole blood, urine, a fecal specimen, plasma, or serum). In particular embodiments, the biological sample is whole blood.

In some embodiments, the donor fluorophore is a terbium cryptate.

In some embodiments, the acceptor fluorophore is selected from the group consisting of fluorescein-like (green zone), Cy5, DY-647, Alexa Fluor 488, Alexa Fluor 546, Alexa Fluor 647, allophycocyanin (APC), and phycoerythrin (PE).

In some embodiments, the first acceptor fluorophore is Alexa Fluor 488 and the second acceptor fluorophore is Alexa Fluor 546. In some embodiments, the first acceptor fluorophore is Alexa Fluor 488 and the second acceptor fluorophore is Alexa Fluor 647. In some embodiments, the first acceptor fluorophore is Alexa Fluor 546 and the second acceptor fluorophore is Alexa Fluor 647.

In some embodiments, the methods described herein further comprise detecting the presence or amount of an additional biomarker. To detect the additional biomarker, the methods comprise contacting the sample with an additional antibody, which binds to a first epitope of the additional biomarker, wherein the additional antibody is labeled with a third donor fluorophore;

contacting the sample with a further antibody, which binds to a second epitope of the additional biomarker, wherein the further antibody is labeled with a third acceptor fluorophore;

incubating the sample for a time sufficient to obtain dual labeled additional biomarker; and exciting the sample having dual labeled additional biomarker using a light source to detect two fluorescence emission signals associated with fluorescence resonance energy transfer (FRET), wherein the first, second, and third acceptor fluorophores are different.

In some embodiments, the light source provides an excitation wavelength between about 300 nm to about 400 nm. In some embodiments, the fluorescence emission signals emit emission wavelengths that are between about 450 nm to 700 nm.

In some embodiments, the concentration of VCAM-1 in the blood is about 100 ng/mL to about 1500 ng/mL. In some embodiments, the normal concentration of VCAM-1 in the blood is about 100 ng/mL to about 500 ng/mL. In some embodiments, an elevated concentration of VCAM-1 in the blood is at least above 550 ng/mL. In some embodiments, an elevated concentration of VCAM-1 in the blood is at least above 650 ng/mL.

In some embodiments, the concentration of A2M in the blood is about 0.1 mg/mL to about 10 mg/mL. In some embodiments, the normal concentration of A2M in the blood is about 1 mg/mL to about 5 mg/mL. In some embodiments, an elevated concentration of A2M in the blood is at least above 5.5 mg/mL. In some embodiments, an elevated concentration of A2M in the blood is at least above 6.5 mg/mL.

These and other aspects, objects and embodiments will become more apparent when read with the detailed description and figures that follow.

BRIEF DESCRIPTION OF THE DRAWINGS

FIG. 2J shows that the multiplexed VCAM-1 results overlay with the single plex VCAM-1 results while A2M results do not show a dose response. Similarly, FIG. 2K shows that the multiplexed A2M results overlay with the single plex A2M results while VCAM-1 results do not show a dose response.

DETAILED DESCRIPTION

I. Definitions

Figure 1:
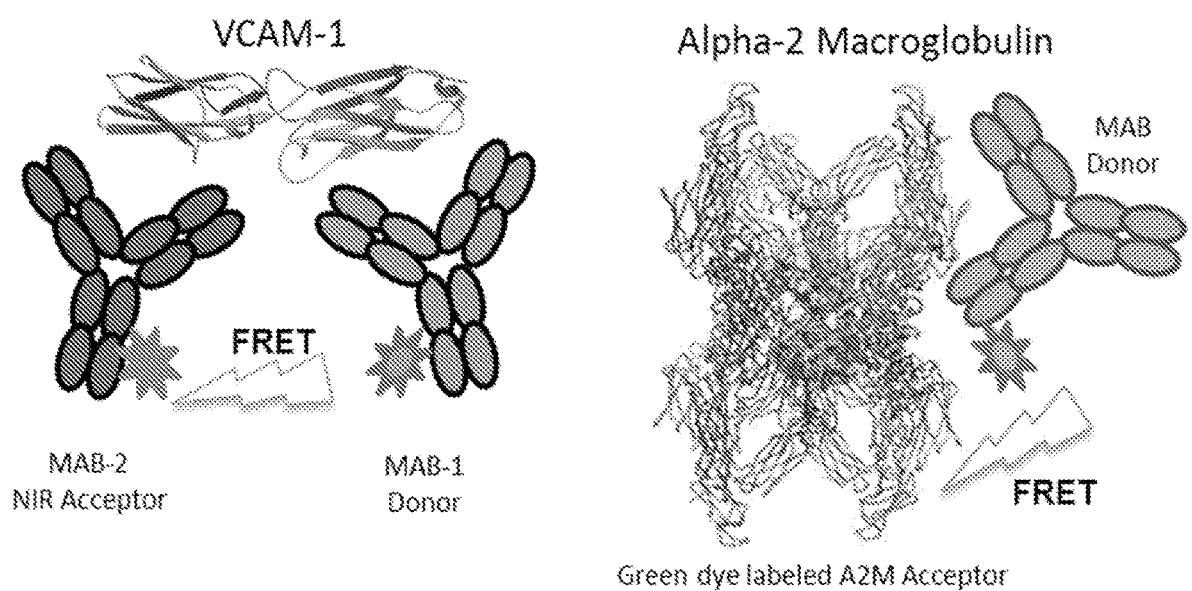
FIG. 1 illustrates one embodiment of the present disclosure.

The terms "a," "an," or "the" as used herein not only includes aspects with one member, but also includes aspects with more than one member.

The term "about" as used herein to modify a numerical value indicates a defined range around that value. If "X" were the value, "about X" would indicate a value from 0.9X to 1.1X, and more preferably, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

When the modifier "about" is applied to describe the beginning of a numerical range, it applies to both ends of the range. Thus, "from about 500 to 850 nm" is equivalent to "from about 500 nm to about 850 nm." When "about" is applied to describe the first value of a set of values, it applies to all values in that set. Thus, "about 580, 700, or 850 nm" is equivalent to "about 580 nm, about 700 nm, or about 850 nm."

"Activated acyl" as used herein includes a —C(O)-LG group. "Leaving group" or "LG" is a group that is susceptible to displacement by a nucleophilic acyl substitution (i.e., a nucleophilic addition to the carbonyl of —C(O)-LG, followed by elimination of the leaving group). Representative leaving groups include halo, cyano, azido, carboxylic acid derivatives such as t-butylcarboxy, and carbonate derivatives such as i-BuOC(O)O—. An activated acyl group may also be an activated ester as defined herein or a carboxylic acid activated by a carbodiimide to form an anhydride (preferentially cyclic) or mixed anhydride —OC(O)$R^a$ or —OC(N$R^a$)NH$R^b$ (preferably cyclic), wherein $R^a$ and $R^b$ are members independently selected from the group consisting of $C_1$-$C_6$ alkyl, $C_1$-$C_6$ perfluoroalkyl, $C_1$-$C_6$ alkoxy, cyclohexyl, 3-dimethylaminopropyl, or N-morpholinoethyl. Preferred activated acyl groups include activated esters.

"Activated ester" as used herein includes a derivative of a carboxyl group that is more susceptible to displacement by nucleophilic addition and elimination than an ethyl ester group (e.g., an NHS ester, a sulfo-NHS ester, a PAM ester, or a halophenyl ester). Representative carbonyl substituents of activated esters include succinimidyloxy (—OC$_4$H$_4$NO$_2$), sulfosuccinimidyloxy (—OC$_4$H$_3$NO$_2$SO$_3$H), -1-oxybenzotriazolyl (—OC$_6$H$_4$N$_3$); 4-sulfo-2,3,5,6-tetrafluorophenyl; or an aryloxy group that is optionally substituted one or more times by electron-withdrawing substituents such as nitro, fluoro, chloro, cyano, trifluoromethyl, or combinations thereof (e.g., pentafluorophenyloxy, or 2,3,5,6-tetrafluorophenyloxy). Preferred activated esters include succinimidyloxy, sulfosuccinimidyloxy, and 2,3,5,6-tetrafluorophenyloxy esters.

"FRET partners" refers to a pair of fluorophores consisting of a donor fluorescent compound such as cryptate and an acceptor compound such as Alexa 647, when they are in proximity to one another and when they are excited at the excitation wavelength of the donor fluorescent compound, these compounds emit a FRET signal. It is known that, in order for two fluorescent compounds to be FRET partners, the emission spectrum of the donor fluorescent compound must partially overlap the excitation spectrum of the acceptor compound. The preferred FRET-partner pairs are those for which the value R0 (Förster distance, distance at which energy transfer is 50% efficient) is greater than or equal to 30 Å.

"FRET signal" refers to any measurable signal representative of FRET between a donor fluorescent compound and an acceptor compound. A FRET signal can therefore be a variation in the intensity or in the lifetime of luminescence of the donor fluorescent compound or of the acceptor compound when the latter is fluorescent.

VCAM-1 (vascular cell adhesion protein 1, CD106, INCAM-110) refers to a cell surface sialoglycoprotein expressed by cytokine activated endothelium. VCAM-1 has a number of functions including the regulation of leukocyte migration, leukocyte-endothelial cell adhesion and signal transduction and may play a role in a number of inflammatory diseases. VCAM-1 is distributed across non-leukocyte and leukocyte cells. VCAM-1 is a member of the Ig superfamily of adhesion molecules, is expressed at high levels on cytokine stimulated vascular endothelial cells, and at minimal levels on unstimulated endothelial cells. VCAM-1 is also present on follicular and inter-follicular dendritic cells of lymph nodes, myoblasts, and some macrophages. VCAM-1_HUMAN, accession P19320 is SEQ ID NO: 1. VCAM-1 has 739 amino acids and a mass of 81,276 Da. This isoform has been chosen as the 'canonical' sequence.

A2M (alpha-2-macroglobulin) refers to a plasma protein found in the blood that mainly acts as an antiprotease and is able to inactivate a variety of proteinases. For example, it functions as an inhibitor of fibrinolysis by inhibiting plasmin and kallikrein. It functions as an inhibitor of coagulation by inhibiting thrombin. Further, A2M sometimes acts as a carrier protein because it also binds to numerous growth factors and cytokines, such as platelet-derived growth factor, basic fibroblast growth factor, TGF-β, insulin, and IL-113. A2M is mainly produced by the liver, and also locally synthesized by macrophages, fibroblasts, and adrenocortical cells. In humans it is encoded by the A2M gene. A2M HUMAN, accession P01023 is SEQ ID NO: 2. A2M has 1474 amino acids and a mass of approximately 720 kDa.

II. Embodiments

The present disclosure provides a homogenous solution phase time-resolved FRET assay (TR-FRET) to detect VCAM-1 and A2M presence or levels in a biological sample such as whole blood. In conjunction with other markers levels, VCAM-1 and A2M can be used as an aid in determination of fibrosis in liver diseases such as NASH, Hepatitis C and Hepatitis B. Forster resonance energy transfer or fluorescence resonance energy transfer (FRET) is a process in which a donor molecule in an excited state transfers its excitation energy through dipole-dipole coupling to an acceptor fluorophore, when the two molecules are brought into close proximity, typically less than 10 nm such as, <9 nm, <8 nm, <7 nm, <6 nm, <5 nm, <4 nm, <3 nm, <2 nm, or less than <1 nm. Upon excitation at a characteristic wavelength, the energy absorbed by the donor is transferred to the acceptor, which in turn emits the energy. The level of light emitted from the acceptor fluorophore is proportional to the degree of donor acceptor complex formation.

Biological materials are typically prone to autofluorescence, which can be minimized by utilizing time-resolved fluorometry (TRF). TRF takes advantage of unique rare earth elements such as lanthanides, (e.g., europium and terbium), which have exceptionally long fluorescence emission half-lives. Time-resolved FRET (TR-FRET) unites the properties of TRF and FRET, which is especially advantageous when analyzing biological samples. If one anti-VCAM-1 antibody is labeled with a donor fluorophore and a second anti-VCAM-1 antibody is labeled with an acceptor fluorophore, and an anti-A2M antibody is labeled with a donor fluorophore (or an acceptor fluorophore) and an isolated A2M protein is labeled with an acceptor fluorophore (or a donor fluorophore), in which the two acceptor fluorophores are different, TR-FRET can occur in the presence of VCAM-1 in the sample and the presence of A2M in the sample would disrupt TR-FRET signal associated with the anti-A2M antibody binding to the isolated A2M protein (FIG. 1).

The use of the FRET phenomenon for studying biological processes implies that each member of the pair of FRET partners will be conjugated to compounds that will interact with one another, and thus bring the FRET partners into close proximity with one another. Upon exposure to light, the FRET partners will generate a FRET signal. In the methods according to the disclosure, an energy donor and an energy acceptor are each conjugated to a different anti-VCAM-1 antibody. An energy donor or an energy acceptor is conjugated to an anti-A2M antibody. Further, an energy donor or an energy acceptor is conjugated to an isolated A2M protein. For example, two anti-VCAM-1 antibodies that bind to two different epitopes in VCAM-1, and an anti-A2M antibody that bind to an epitope in A2M can be used. The energy transfer between the two FRET partners depends upon each binding to the analyte. Förster or fluorescence resonance energy transfer (FRET), is a physical phenomenon in which a donor fluorophore in its excited state non-radiatively transfers its excitation energy to a neighboring acceptor fluorophore, thereby causing the acceptor to emit its characteristic fluorescence.

As such, in one aspect, the present disclosure provides an assay method for detecting the presence or amount of VCAM-1 and A2M in a sample, the method comprising:

contacting the sample with a first anti-VCAM-1 antibody, which binds to a first epitope of VCAM-1, wherein the first anti-VCAM-1 antibody is labeled with a first donor fluorophore;

contacting the sample with a second anti-VCAM-1 antibody, which binds to a second epitope of VCAM-1, wherein the second anti-VCAM-1 antibody is labeled with a first acceptor fluorophore;

contacting the sample with an anti-A2M antibody, which binds to an epitope of A2M, wherein the anti-A2M antibody is labeled with a second donor fluorophore;

contacting the sample with an isolated A2M protein, wherein the isolated A2M protein is labeled with a second acceptor fluorophore;

incubating the sample for a time sufficient to obtain dual labeled VCAM-1 and labeled A2M; and exciting the sample having dual labeled VCAM-1 and labeled A2M using one or more light sources to detect at least one fluorescence emission signal associated with fluorescence resonance energy transfer (FRET), wherein the first and second acceptor fluorophores are different.

In another aspect, the present disclosure provides an assay method for detecting the presence or amount of VCAM-1 and A2M in a sample, the method comprising:

contacting the sample with a first anti-VCAM-1 antibody, which binds to a first epitope of VCAM-1, wherein the first anti-VCAM-1 antibody is labeled with a first donor fluorophore;

contacting the sample with a second anti-VCAM-1 antibody, which binds to a second epitope of VCAM-1, wherein the second anti-VCAM-1 antibody is labeled with a first acceptor fluorophore;

contacting the sample with an anti-A2M antibody, which binds to an epitope of A2M, wherein the anti-A2M antibody is labeled with a second acceptor fluorophore;

contacting the sample with an isolated A2M protein, wherein the isolated A2M protein is labeled with a second donor fluorophore;

incubating the sample for a time sufficient to obtain dual labeled VCAM-1 and labeled A2M; and exciting the sample having dual labeled VCAM-1 and labeled A2M using one or more light sources to detect at least one fluorescence emission signal associated with fluorescence resonance energy transfer (FRET), wherein the first and second acceptor fluorophores are different.

In some embodiments, the first and second donor fluorophores are the same and the sample is excited using one light source. In other embodiments of this aspect of the disclosure, the first and second donor fluorophores are different and the sample is excited using two different light sources.

In this aspect of the disclosure, two anti-VCAM-1 antibodies, one labeled with a donor fluorophore and one labeled with an acceptor fluorophore, are used. The two anti-VCAM-1 antibodies bind to two different epitopes on VCAM-1. An anti-A2M antibody labeled with a donor fluorophore (or an acceptor fluorophore) and an isolated A2M protein labeled with an acceptor fluorophore (or a donor fluorophore) are also used. The two anti-VCAM-1 antibodies binding to two different epitopes on VCAM-1 bring the first donor fluorophore and the first acceptor fluorophore in proximity to each other. The anti-A2M antibody and the isolated A2M protein to bring the second donor fluorophore and the second acceptor fluorophore in proximity to each other. The donor fluorophore in its excited state can transfer its excitation energy to the acceptor fluorophore to cause the acceptor fluorophore to emit its characteristic fluorescence. In some embodiments, the two acceptor fluorophores are different and emit fluorescence at different wavelengths. Thus, the appearance of the fluorescence emission signal is proportional to the presence or level of VCAM-1 in the sample and the disappearance of the fluorescence emission signal is proportional to the presence or level of A2M in the sample.

In some embodiments of the two aspects of the disclosure described above, the methods described herein further comprise detecting the presence or amount of an additional biomarker. To detect the additional biomarker, the methods comprise:

contacting the sample with an additional antibody, which binds to a first epitope of the additional biomarker, wherein the additional antibody is labeled with a third donor fluorophore;

contacting the sample with a further antibody, which binds to a second epitope of the additional biomarker, wherein the further antibody is labeled with a third acceptor fluorophore;

incubating the sample for a time sufficient to obtain dual labeled additional biomarker; and exciting the sample having dual labeled additional biomarker using a light source to detect two fluorescence emission signals associated with fluorescence resonance energy transfer (FRET), wherein the first, second, and third acceptor fluorophores are different.

In some embodiments, the first acceptor fluorophore is Alexa Fluor 488, the second acceptor fluorophore is Alexa Fluor 546, and the third acceptor fluorophore is Alexa Fluor 647.

In addition to VCAM-1 and A2M, the additional biomarker that can be detected using the methods described herein can be selected from the group consisting of M65 (CK18 full-length), ICAM-1, eSelectin, syndecan1 (CD138), adiponectin, chitinase-3-like-1 (YKL40), ACY1, osteopontin, GDF15, cathepsin D, M30 (CK18 fragment), ANGPTL4, FGF21, THBS2, MMP2, ANGPTL3, HA (hyaluronic acid), IP10, VAP1, MCP1, IL2Rα, EMMPRIN, FABP1, IL6, angiopoietin1, collagen IV-α1, FGF19, VEGF, galectin1, galectin3, MMP1, MMP9, haptoglobin, TIMP1, resistin, galectin3BP, e-cadherin, ApoA1, galectin 9, HBEGF, and MMP3. In some embodiments, the additional biomarker is ANGPTL4, FGF21, THBS2, MMP2, ANGPTL3, or HA (hyaluronic acid). In some embodiments, the additional biomarker is IP10, VAP1, MCP1, IL2Rα, EMMPRIN, or FABP1. In some embodiments, the additional biomarker is IL6, angiopoietin1, collagen IV-α1, FGF19, VEGF, or galectin1. In some embodiments, the additional biomarker is galectin3, MMP1, MMP9, haptoglobin, TIMP1, or resistin. In some embodiments, the additional biomarker is galectin3BP, e-cadherin, ApoA1, galectin 9, HBEGF, or MMP3.

In certain aspects, the FRET assay is a time-resolved FRET assay. The fluorescence emission signal or measured FRET signal is directly correlated with the biological phenomenon studied. In fact, the level of energy transfer between the donor fluorescent compound and the acceptor fluorescent compound is proportional to the reciprocal of the distance between these compounds to the $6^{th}$ power. For the donor/acceptor pairs commonly used by those skilled in the art, the distance Ro (corresponding to a transfer efficiency of 50%) is in the order of 1, 5, 10, 20 or 30 nanometers.

In certain aspects, the sample is a biological sample. Suitable biological samples include, but are not limited to, whole blood, urine, a fecal specimen, plasma or serum. In a preferred aspect, the biological sample is whole blood.

In certain aspects, the FRET energy donor compound is a cryptate, such as a lanthanide cryptate.

Figure 5:
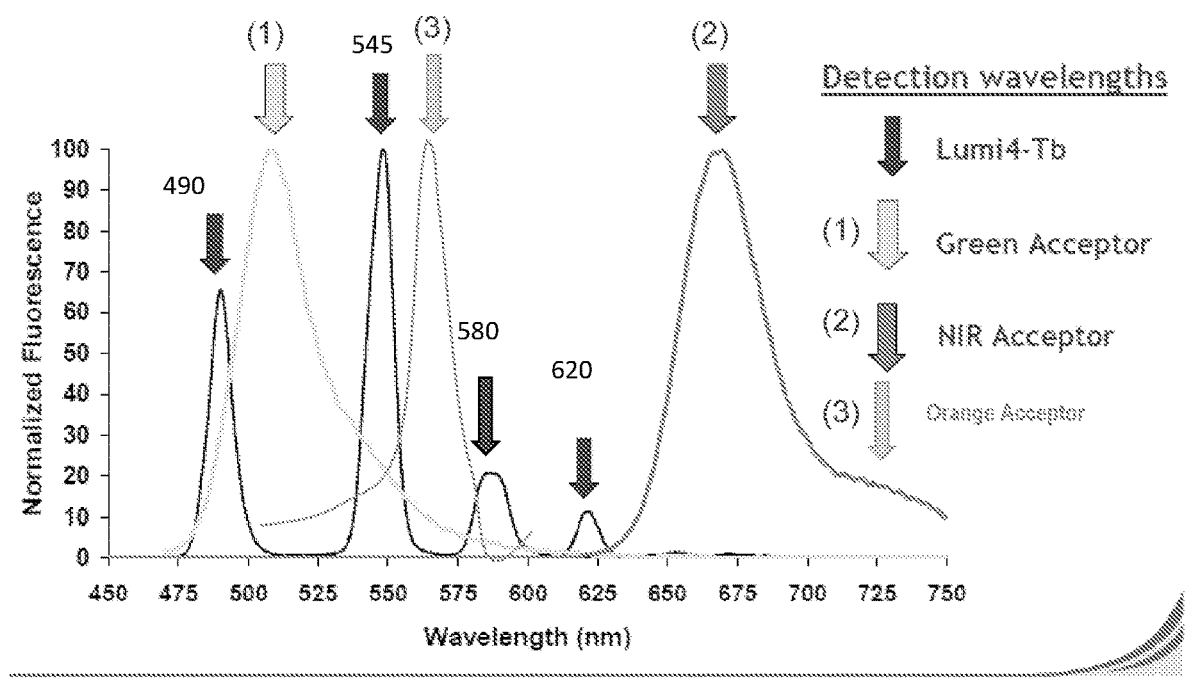
FIG. 5 illustrates donor and acceptor wavelengths in one embodiment of the present disclosure.

In certain aspects, the cryptate has an absorption wavelength between about 300 nm to about 400 nm such as about 325 nm to about 375 nm. In certain aspects, as shown in FIG. 5, cyptate dyes (Lumi4-Tb in FIG. 5) have four fluorescence emission peaks at about 490 nm, about 548 nm, about 587 nm, and 621 nm. Thus, as a donor, the cryptate is compatible with fluorescein-like (green zone) and Cy5 or DY-647-like (red zone) acceptor (e.g., green acceptor, NIR acceptor, or orange acceptor in FIG. 5) to perform TR-FRET experiments.

In certain aspects, the introduction of a time delay between a flash excitation and the measurement of the fluorescence at the acceptor emission wavelength allows to discriminate long lived from short-lived fluorescence and to increase signal-to-noise ratio.

Cryptates as FRET Donors

In certain aspects, the terbium cryptate molecule "Lumi4-Tb" from Lumiphore, marketed by Cisbio bioassays is used as the cryptate donor. The terbium cryptate "Lumi4-Tb" having the formula below, which can be coupled to an antibody by a reactive group, in this case, for example, an NHS ester:

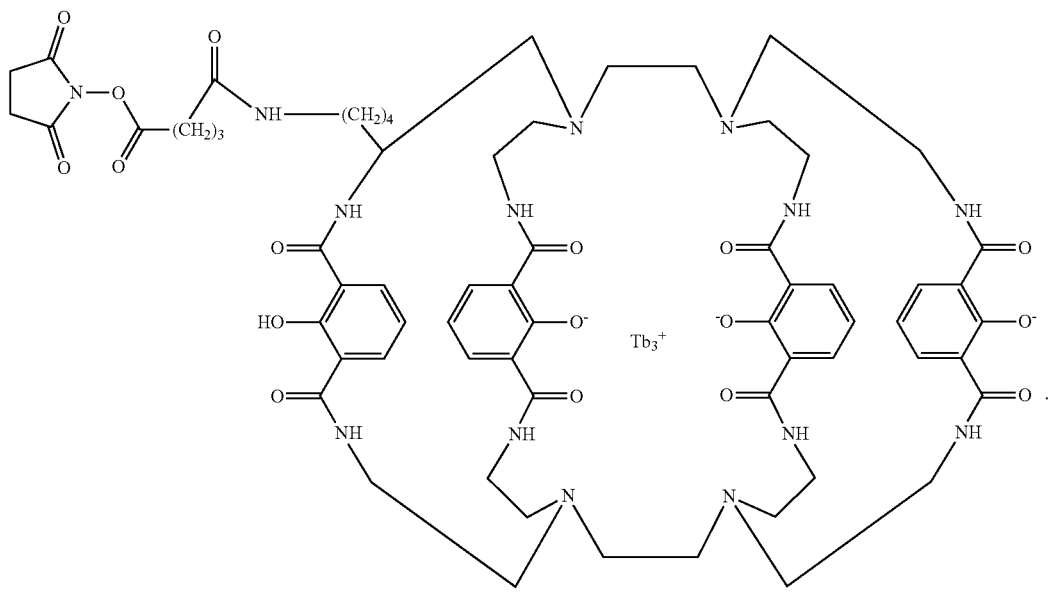

An activated ester (an NHS ester) can react with a primary amine on an antibody to make a stable amide bond. A maleimide on the cryptate and a thiol on the antibody can react together and make a thioether. Alkyl halides react with amines and thiols to make alkylamines and thioethers, respectively. Any derivative providing a reactive moiety that can be conjugated to a antibody can be utilized herein. For example, in some embodiments, when an anti-VCAM-1 antibody or an anti-A2M antibody is used, the maleimide on the cryptate can react with a thiol on the antibody.

In certain other aspects, cryptates disclosed in WO2015157057, titled "Macrocycles" are suitable for use in the present disclosure. This publication contains cryptate molecules useful for labeling biomolecules. As disclosed therein, certain of the cryptates have the structure:

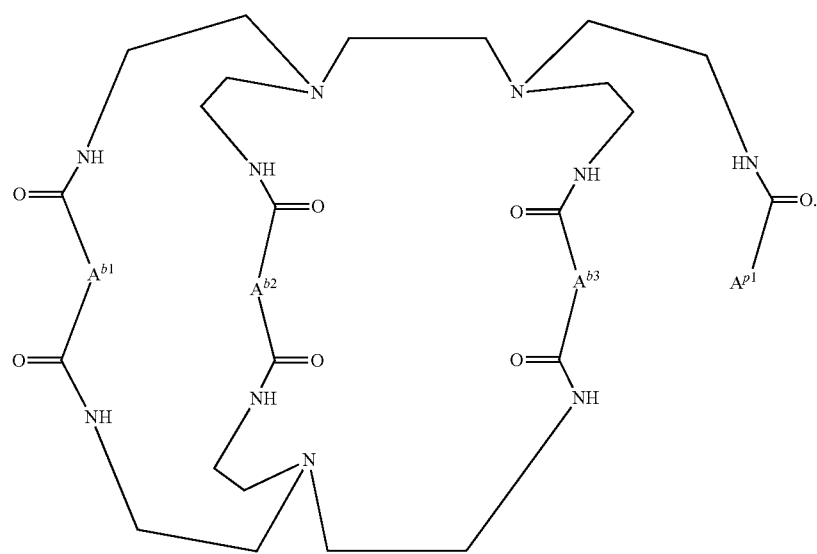
In certain other aspects, a terbium cryptate useful in the present disclosure is shown below:
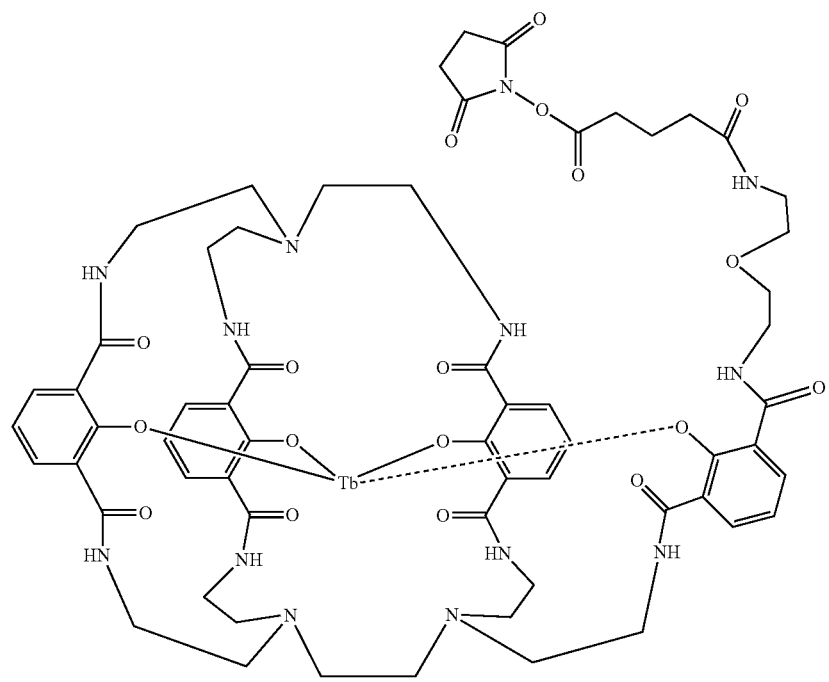

In certain aspects, the cryptates that are useful in the present invention are disclosed in WO 2018/130988, published Jul. 19, 2018. As disclosed therein, the compounds of Formula I are useful as FRET donors in the present disclosure:

(Formula I)

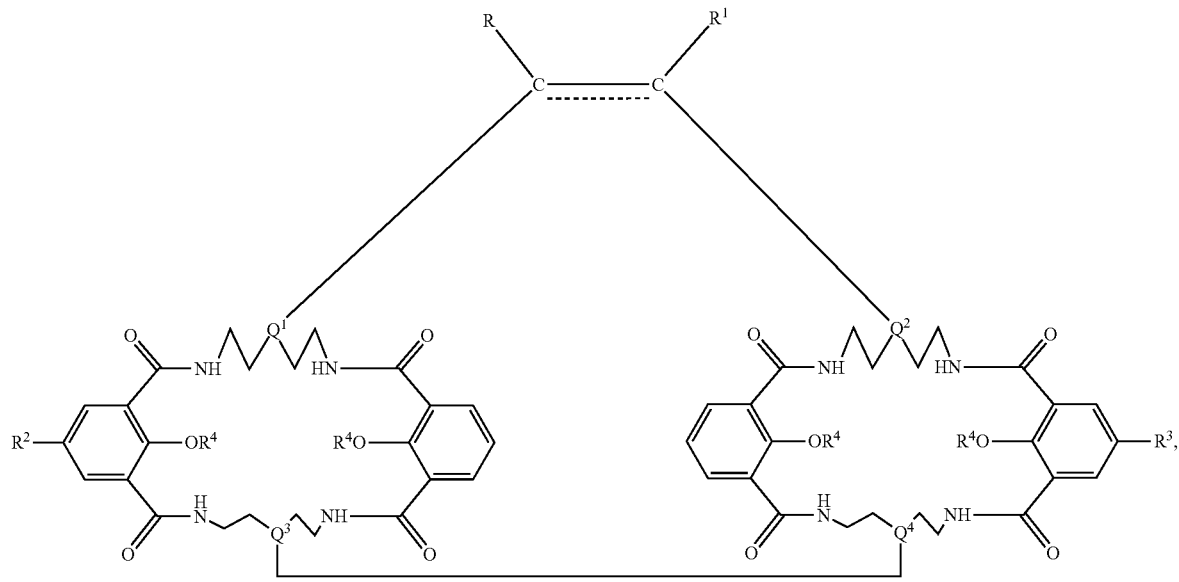

wherein when the dotted line is present, R and IV are each independently selected from the group consisting of hydrogen, halogen, hydroxyl, alkyl optionally substituted with one or more halogen atoms, carboxyl, alkoxycarbonyl, amido, sulfonato, alkoxycarbonylalkyl or alkylcarbonylalkoxy or alternatively, R and R' join to form an optionally substituted cyclopropyl group wherein the dotted bond is absent;
$R^2$ and $R^3$ are each independently a member selected from the group consisting of hydrogen, halogen, $SO_3H$, $-SO_2-X$, wherein X is a halogen, optionally substituted alkyl, optionally substituted aryl, optionally substituted alkenyl, optionally substituted alkynyl, optionally substituted cycloalkyl, or an activated group that can be linked to a biomolecule, wherein the activated group is a member selected from the group consisting of a halogen, an activated ester, an activated acyl, optionally substituted alkylsulfonate ester, optionally substituted arylsulfonate ester, amino, formyl, glycidyl, halo, haloacetamidyl, haloalkyl, hydrazinyl, imido ester, isocyanato, isothiocyanato, maleimidyl, mercapto, alkynyl, hydroxyl, alkoxy, amino, cyano, carboxyl, alkoxycarbonyl, amido, sulfonato, alkoxycarbonylalkyl, cyclic anhydride, alkoxyalkyl, a water solubilizing group or L;
$R^4$ are each independently a hydrogen, $C_1$-$C_6$ alkyl, or alternatively, 3 of the $R^4$ groups are absent and the resulting oxides are chelated to a lanthanide cation; and
$Q^1$-$Q^4$ are each independently a member selected from the group of carbon or nitrogen.

FRET Acceptors

Figure 3:
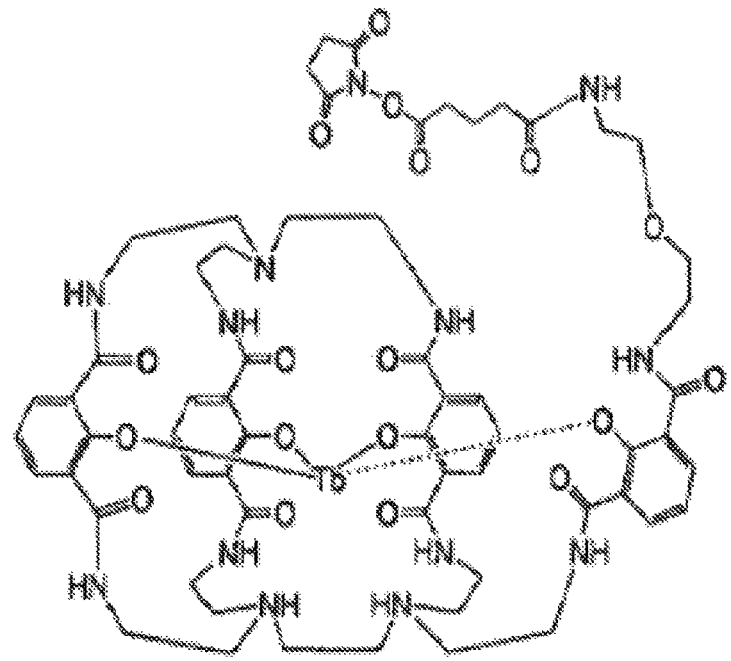
FIG. 3 illustrates one embodiment of a donor fluorophore of the present disclosure.
Figure 4:
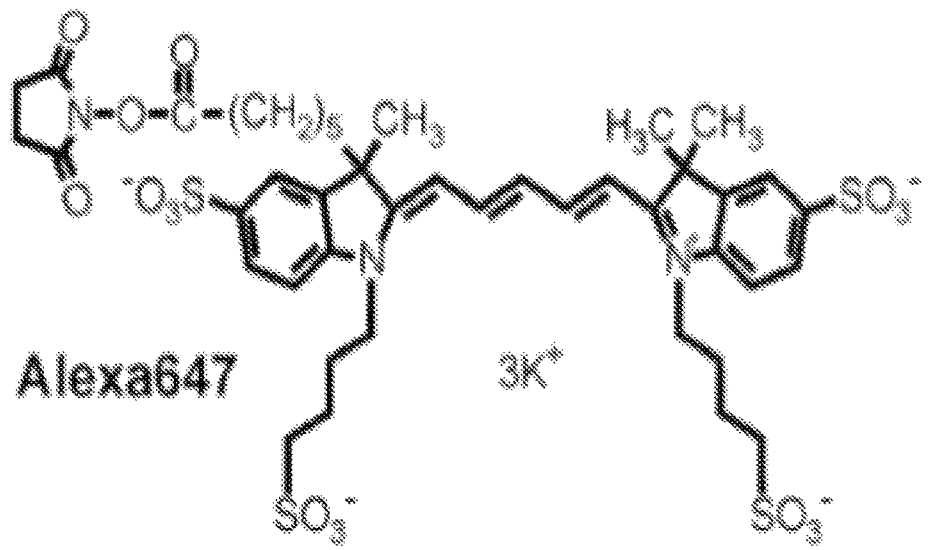
FIG. 4 illustrates one embodiment of an acceptor fluorophore of the present disclosure.

In order to detect a FRET signal, a FRET acceptor is required. The FRET acceptor has an excitation wavelength that overlaps with an emission wavelength of the FRET donor. In the present disclosure, two FRET signals of the acceptors are detected with one FRET signal proportional to the concentration level of VCAM-1 present in the sample (e.g., a patient's blood sample) and the other FRET signal inversely proportional to the concentration level of A2M present in the sample (e.g., a patient's blood sample). A known amount of calibrators, i.e., standard curves (FIGS. 2A-2D), can be used to interpolate the concentration levels of VCAM-1 and A2M. As described above, when an anti-VCAM-1 or anti-A2M antibody is used, the cryptate donor (FIG. 3) can be used to label the antibody. Lumi4-Tb has 3 spectrally distinct peaks, at 490, 550 and 620 nm, which can be used for energy transfer (FIG. 5). Subsequently, a first acceptor can be used to label an anti-VCAM-1 antibody (which can bind to a different epitope on VCAM-1 from the epitope on VCAM-1 bound by the first anti-VCAM-1 antibody). A second acceptor can be used to label an anti-A2M antibody. In the present disclosure, the first acceptor and the second acceptor are different and emit two fluorescence emission signals at different emission wavelengths. The acceptor molecules that can be used include, but are not limited to, fluorescein-like (green zone), Cy5, DY-647, Alexa Fluor 488, Alexa Fluor 546, Alexa Fluor 647 (FIG. 4), allophycocyanin (APC), and phycoerythrin (PE). Donor and acceptor fluorophores can be conjugated using a primary amine on an antibody.

Other acceptors include, but are not limited to, cyanin derivatives, D2, CY5, fluorescein, coumarin, rhodamine, carbopyronine, oxazine and its analogs, Alexa Fluor fluorophores, Crystal violet, perylene bisimide fluorophores, squaraine fluorophores, boron dipyrromethene derivatives, NBD (nitrobenzoxadiazole) and its derivatives, DABCYL (4-((4-(dimethylamino)phenyl)azo)benzoic acid), allophycocyanin (APC), and phycoerythrin (PE).

In one aspect, fluorescence can be characterized by wavelength, intensity, lifetime, and polarization.

Antibodies

In one aspect, a human anti-VCAM-1/CD106 antibody (e.g., Catalog #MAB809 (R&D systems), from monoclonal mouse $IgG_1$ Clone #HAE-2Z and shown to be specific for human VCAM-1/CD106) can be used to conjugate to a donor fluorophore (e.g., cryptate) and a different human anti-VCAM-1/CD106 antibody (e.g., Catalog #MA5-16429 (Thermo Fisher Scientific), from monoclonal mouse IgG1 Clone #1.G11B1) can be used to conjugate to an acceptor fluorophore, or vice versa. Other commercial anti-VCAM-1 antibodies are available in the art. A human anti-A2M antibody (e.g., Catalog #10C-CR2005M1 (Fitzgerald Industries International, Inc), from monoclonal mouse $IgG_1$ Clone #3127485 and shown to be specific for human A2M) can be used to conjugate to a donor fluorophore (e.g., cryptate) and an isolated A2M protein (e.g., Catalog #ab77935 (Abcam), from human plasma) can be used to conjugate to an acceptor fluorophore, or vice versa. Other commercial anti-A2M antibodies are available in the art.

The methods herein for detecting the presence or levels of VCAM-1 and A2M can use a variety of samples, which include a tissue sample, blood, biopsy, serum, plasma, saliva, urine, or stool sample.

Production of Antibodies

The generation and selection of antibodies not already commercially available can be accomplished several ways. For example, one way is to express and/or purify a polypeptide of interest (i.e., antigen) using protein expression and purification methods known in the art, while another way is to synthesize the polypeptide of interest using solid phase peptide synthesis methods known in the art. See, e.g., *Guide to Protein Purification*, Murray P. Deutcher, ed., *Meth. Enzymol.*, Vol. 182 (1990); *Solid Phase Peptide Synthesis*, Greg B. Fields, ed., *Meth. Enzymol.*, Vol. 289 (1997); Kiso et al., *Chem. Pharm. Bull.*, 38:1192-99 (1990); Mostafavi et al., *Biomed. Pept. Proteins Nucleic Acids*, 1:255-60, (1995); and Fujiwara et al., *Chem. Pharm. Bull.*, 44:1326-31 (1996). The purified or synthesized polypeptide can then be injected, for example, into mice or rabbits, to generate polyclonal or monoclonal antibodies. One skilled in the art will recognize that many procedures are available for the production of antibodies, for example, as described in Antibodies, *A Laboratory Manual*, Harlow and Lane, Eds., Cold Spring Harbor Laboratory, Cold Spring Harbor, N.Y. (1988). One skilled in the art will also appreciate that binding fragments or Fab fragments which mimic antibodies can also be prepared from genetic information by various procedures (see, e.g., *Antibody Engineering: A Practical Approach*, Borrebaeck, Ed., Oxford University Press, Oxford (1995); and Huse et al., *J. Immunol.*, 149:3914-3920 (1992)).

In addition, numerous publications have reported the use of phage display technology to produce and screen libraries of polypeptides for binding to a selected target antigen (see, e.g, Cwirla et al., *Proc. Natl. Acad. Sci. USA*, 87:6378-6382 (1990); Devlin et al., *Science*, 249:404-406 (1990); Scott et al., *Science*, 249:386-388 (1990); and Ladner et al., U.S. Pat. No. 5,571,698). A basic concept of phage display methods is the establishment of a physical association between a polypeptide encoded by the phage DNA and a target antigen. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target antigen bind to the target antigen and these phage are enriched by affinity screening to the target antigen. The identity of polypeptides displayed from these phage can be determined from their respective genomes. Using these methods, a polypeptide identified as having a binding affinity for a desired target antigen can then be synthesized in bulk by conventional means (see, e.g., U.S. Pat. No. 6,057, 098).

The antibodies that are generated by these methods can then be selected by first screening for affinity and specificity with the purified polypeptide antigen of interest and, if required, comparing the results to the affinity and specificity of the antibodies with other polypeptide antigens that are desired to be excluded from binding. The screening procedure can involve immobilization of the purified polypeptide antigens in separate wells of microtiter plates. The solution containing a potential antibody or group of antibodies is then placed into the respective microtiter wells and incubated for about 30 minutes to 2 hours. The microtiter wells are then washed and a labeled secondary antibody (e.g., an anti-mouse antibody conjugated to alkaline phosphatase if the raised antibodies are mouse antibodies) is added to the wells and incubated for about 30 minutes and then washed. Substrate is added to the wells and a color reaction will appear where antibody to the immobilized polypeptide antigen is present.

The antibodies so identified can then be further analyzed for affinity and specificity. In the development of immunoassays for a target protein (VCAM-1 and/or A2M), the purified target protein acts as a standard with which to judge the sensitivity and specificity of the immunoassay using the antibodies that have been selected. Because the binding affinity of various antibodies may differ, e.g., certain antibody combinations may interfere with one another sterically, assay performance of an antibody may be a more important measure than absolute affinity and specificity of that antibody.

Those skilled in the art will recognize that many approaches can be taken in producing antibodies or binding fragments and screening and selecting for affinity and specificity for the various polypeptides of interest, but these approaches do not change the scope of the present invention.

A. Polyclonal Antibodies

Polyclonal antibodies are preferably raised in animals by multiple subcutaneous (sc) or intraperitoneal (ip) injections of a polypeptide of interest and an adjuvant. It may be useful to conjugate the polypeptide of interest to a protein carrier that is immunogenic in the species to be immunized, such as, e.g., keyhole limpet hemocyanin, serum albumin, bovine thyroglobulin, or soybean trypsin inhibitor using a bifunctional or derivatizing agent. Non-limiting examples of bifunctional or derivatizing agents include maleimidobenzoyl sulfosuccinimide ester (conjugation through cysteine residues), N-hydroxysuccinimide (conjugation through lysine residues), glutaraldehyde, succinic anhydride, $SOCl_2$, and $R_1N=C=NR$, wherein R and $R_1$ are different alkyl groups.

Animals are immunized against the polypeptide of interest or an immunogenic conjugate or derivative thereof by combining, e.g., 100 μg (for rabbits) or 5 μg (for mice) of the antigen or conjugate with 3 volumes of Freund's complete adjuvant and injecting the solution intradermally at multiple sites. One month later, the animals are boosted with about ⅕ to 1/10 the original amount of polypeptide or conjugate in Freund's incomplete adjuvant by subcutaneous injection at multiple sites. Seven to fourteen days later, the animals are bled and the serum is assayed for antibody titer. Animals are typically boosted until the titer plateaus. Preferably, the animal is boosted with the conjugate of the same polypeptide, but conjugation to a different immunogenic protein and/or through a different cross-linking reagent may be used. Conjugates can also be made in recombinant cell culture as fusion proteins. In certain instances, aggregating agents such as alum can be used to enhance the immune response.

B. Monoclonal Antibodies

Monoclonal antibodies are generally obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, monoclonal antibodies can be made using the hybridoma method described by Kohler et al., Nature, 256:495 (1975) or by any recombinant DNA method known in the art (see, e.g., U.S. Pat. No. 4,816,567).

In the hybridoma method, a mouse or other appropriate host animal (e.g., hamster) is immunized as described above to elicit lymphocytes that produce or are capable of producing antibodies which specifically bind to the polypeptide of interest used for immunization. Alternatively, lymphocytes are immunized in vitro. The immunized lymphocytes are then fused with myeloma cells using a suitable fusing agent, such as polyethylene glycol, to form hybridoma cells (see, e.g., Goding, *Monoclonal Antibodies: Principles and Practice*, Academic Press, pp. 59-103 (1986)). The hybridoma cells thus prepared are seeded and grown in a suitable culture medium that preferably contains one or more substances which inhibit the growth or survival of the unfused, parental myeloma cells. For example, if the parental myeloma cells lack the enzyme hypoxanthine guanine phosphoribosyl transferase (HGPRT), the culture medium for the hybridoma cells will typically include hypoxanthine, aminopterin, and thymidine (HAT medium), which prevent the growth of HGPRT-deficient cells.

Preferred myeloma cells are those that fuse efficiently, support stable high-level production of antibody by the selected antibody-producing cells, and/or are sensitive to a medium such as HAT medium. Examples of such preferred myeloma cell lines for the production of human monoclonal antibodies include, but are not limited to, murine myeloma lines such as those derived from MOPC-21 and MPC-11 mouse tumors (available from the Salk Institute Cell Distribution Center; San Diego, Calif.), SP-2 or X63-Ag8-653 cells (available from the American Type Culture Collection; Rockville, Md.), and human myeloma or mouse-human heteromyeloma cell lines (see, e.g., Kozbor, *J. Immunol.*, 133:3001 (1984); and Brodeur et al., *Monoclonal Antibody Production Techniques and Applications*, Marcel Dekker, Inc., New York, pp. 51-63 (1987)).

The culture medium in which hybridoma cells are growing can be assayed for the production of monoclonal antibodies directed against the polypeptide of interest. Preferably, the binding specificity of monoclonal antibodies produced by hybridoma cells is determined by immunoprecipitation or by an in vitro binding assay, such as a radioimmunoassay (RIA) or an enzyme-linked immunoabsorbent assay (ELISA). The binding affinity of monoclonal antibodies can be determined using, e.g., the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (see, e.g., Goding, *Monoclonal Antibodies: Principles and Practice*, Academic Press, pp. 59-103 (1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody, to induce the synthesis of monoclonal antibodies in the recombinant host cells. See, e.g., Skerra et al., *Curr. Opin. Immunol.*, 5:256-262 (1993); and Pluckthun, *Immunol Rev.*, 130:151-188 (1992). The DNA can also be modified, for example, by substituting the coding sequence for human heavy chain and light chain constant domains in place of the homologous murine sequences (see, e.g., U.S. Pat. No. 4,816,567; and Morrison et al., *Proc. Natl. Acad. Sci. USA*, 81:6851 (1984)), or by covalently joining to the immunoglobulin coding sequence all or part of the coding sequence for a non-immunoglobulin polypeptide.

In a further embodiment, monoclonal antibodies or antibody fragments can be isolated from antibody phage libraries generated using the techniques described in, for example, McCafferty et al., *Nature*, 348:552-554 (1990); Clackson et al., *Nature*, 352:624-628 (1991); and Marks et al., *J. Mol. Biol.*, 222:581-597 (1991). The production of high affinity (nM range) human monoclonal antibodies by chain shuffling is described in Marks et al., *BioTechnology*, 10:779-783 (1992). The use of combinatorial infection and in vivo recombination as a strategy for constructing very large phage libraries is described in Waterhouse et al., *Nuc. Acids Res.*, 21:2265-2266 (1993). Thus, these techniques are viable alternatives to traditional monoclonal antibody hybridoma methods for the generation of monoclonal antibodies. Human Antibodies As an alternative to humanization, human antibodies can be generated. In some embodiments, transgenic animals (e.g., mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immun.*, 7:33 (1993); and U.S. Pat. Nos. 5,591,669, 5,589,369, and 5,545,807.

Alternatively, phage display technology (see, e.g., McCafferty et al., *Nature*, 348:552-553 (1990)) can be used to produce human antibodies and antibody fragments in vitro, using immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a singlestranded DNA copy of the phage genome, selections based on the functional properties of the antibody also result in selection of the gene encoding the antibody exhibiting those properties. Thus, the phage mimics some of the properties of the B cell. Phage display can be performed in a variety of formats as described in, e.g., Johnson et al., *Curr. Opin. Struct. Biol.*, 3:564-571 (1993). Several sources of V-gene segments can be used for phage display. See, e.g., Clackson et al., *Nature*, 352:624-628 (1991). A repertoire of V genes from unimmunized human donors can be constructed and antibodies to a diverse array of antigens (including self-antigens) can be isolated essentially following the techniques described in Marks et al., *J. Mol. Biol.*, 222:581-597 (1991); Griffith et al., *EMBO J.*, 12:725-734 (1993); and U.S. Pat. Nos. 5,565,332 and 5,573,905.

In certain instances, human antibodies can be generated by in vitro activated B cells as described in, e.g., U.S. Pat. Nos. 5,567,610 and 5,229,275.

C. Antibody Fragments

Various techniques have been developed for the production of antibody fragments. Traditionally, these fragments were derived via proteolytic digestion of intact antibodies (see, e.g., Morimoto et al., *J. Biochem. Biophys. Meth.*, 24:107-117 (1992); and Brennan et al., *Science*, 229:81 (1985)). However, these fragments can now be produced directly using recombinant host cells. For example, the antibody fragments can be isolated from the antibody phage libraries discussed above. Alternatively, Fab'-SH fragments can be directly recovered from *E. coli* cells and chemically coupled to form $F(ab')_2$ fragments (see, e.g., Carter et al., *BioTechnology*, 10:163-167 (1992)). According to another approach, $F(ab')_2$ fragments can be isolated directly from recombinant host cell culture. Other techniques for the production of antibody fragments will be apparent to those skilled in the art. In other embodiments, the antibody of choice is a single chain Fv fragment (scFv). See, e.g., PCT Publication No. WO 93/16185; and U.S. Pat. Nos. 5,571,894 and 5,587,458. The antibody fragment may also be a linear antibody as described, e.g., in U.S. Pat. No. 5,641,870. Such linear antibody fragments may be monospecific or bispecific.

D. Antibody Purification

When using recombinant techniques, antibodies can be produced inside an isolated host cell, in the periplasmic space of a host cell, or directly secreted from a host cell into the medium. If the antibody is produced intracellularly, the particulate debris is first removed, for example, by centrifugation or ultrafiltration. Carter et al., *BioTech.*, 10:163-167 (1992) describes a procedure for isolating antibodies which are secreted into the periplasmic space of *E. coli*. Briefly, cell paste is thawed in the presence of sodium acetate (pH 3.5), EDTA, and phenylmethylsulfonylfluoride (PMSF) for about 30 min. Cell debris can be removed by centrifugation. Where the antibody is secreted into the medium, supernatants from such expression systems are generally concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from cells can be purified using, for example, hydroxylapatite chromatography, gel electrophoresis, dialysis, and affinity chromatography. The suitability of protein A as an affinity ligand depends on the species and isotype of any immunoglobulin Fc domain that is present in the antibody. Protein A can be used to purify antibodies that are based on human γ1, γ2, or γ4 heavy chains (see, e.g., Lindmark et al., *J. Immunol. Meth.*, 62:1-13 (1983)). Protein G is recommended for all mouse isotypes and for human γ3 (see, e.g., Guss et al., *EMBO J.*, 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker; Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

E. Bispecific Antibodies

Bispecific antibodies are antibodies that have binding specificities for at least two different epitopes. Bispecific antibodies can be prepared as full-length antibodies or antibody fragments (e.g., $F(ab')_2$ bispecific antibodies).

Methods for making bispecific antibodies are known in the art. Traditional production of full-length bispecific antibodies is based on the co-expression of two immunoglobulin heavy chain-light chain pairs, where the two chains have different specificities (see, e.g., Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule is usually performed by affinity chromatography. Similar procedures are disclosed in PCT Publication No. WO 93/08829 and Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy chain constant region (CH1) containing the site necessary for light chain binding present in at least one of the fusions. DNA encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains into one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain with a second binding specificity in the other arm. This asymmetric structure facilitates the separation of the desired bispecific compound from unwanted immunoglobulin chain combinations, as the presence of an immunoglobulin light chain in only one half of the bispecific molecule provides for a facile way of separation. See, e.g., PCT Publication No. WO 94/04690 and Suresh et al., *Meth. Enzymol.*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side-chains from the interface of the first antibody molecule are replaced with larger side chains (e.g., tyrosine or tryptophan). Compensatory "cavities" of identical or similar size to the large side-chain(s) are created on the interface of the second antibody molecule by replacing large amino acid side-chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies can be made using any convenient cross-linking method. Suitable cross-linking agents and techniques are well-known in the art, and are disclosed in, e.g., U.S. Pat. No. 4,676,980.

Suitable techniques for generating bispecific antibodies from antibody fragments are also known in the art. For example, bispecific antibodies can be prepared using chemical linkage. In certain instances, bispecific antibodies can be generated by a procedure in which intact antibodies are proteolytically cleaved to generate F(ab')$_2$ fragments (see, e.g., Brennan et al., *Science*, 229:81 (1985)). These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody.

In some embodiments, Fab'-SH fragments can be directly recovered from *E. coli* and chemically coupled to form bispecific antibodies. For example, a fully humanized bispecific antibody F(ab')$_2$ molecule can be produced by the methods described in Shalaby et al., *J. Exp. Med.*, 175: 217-225 (1992). Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. See, e.g., Kostelny et al., *J. Immunol.*, 148:1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy chain variable domain (VH) connected to a light chain variable domain (VL) by a linker which is too short to allow pairing between the two domains on the same chain. Accordingly, the VH and VL domains of one fragment are forced to pair with the complementary VL and VH domains of another fragment, thereby forming two antigen binding sites. Another strategy for making bispecific antibody fragments by the use of single-chain Fv (sFv) dimers is described in Gruber et al., *J. Immunol.*, 152:5368 (1994).

Antibodies with more than two valencies are also contemplated. For example, trispecific antibodies can be prepared. See, e.g., Tutt et al., *J. Immunol.*, 147:60 (1991).

III. Vascular Cell Adhesion Protein 1 (VCAM-1)

VCAM-1 is a transmembrane cellular adhesion protein that mediates the adhesion of lymphocytes, monocytes, eosinophils, and basophils to vascular endothelium. Upregulation of VCAM-1 in endothelial cells by cytokines occurs as a result of increased gene transcription (e.g., in response to Tumor necrosis factor-alpha (TNFα) and Interleukin-1 (IL-1)). VCAM-1 is encoded by the vascular cell adhesion molecule 1 gene (VCAM-1; Entrez GeneID:7412) and is produced after differential splicing of the transcript (Genbank Accession No. NM_001078 (variant 1) or NM_080682 (variant 2)), and processing of the precursor polypeptide splice isoform (Genbank Accession No. NP_001069 (isoform a) or NP_542413 (isoform b)).

The human VCAM-1 polypeptide sequence is set forth in, e.g., Genbank Accession No. NP_001069. The human VCAM-1 mRNA (coding) sequence is set forth in, e.g., Genbank Accession No. NM_001078. One skilled in the art will appreciate that VCAM-1 is also known as VCAM-1, V-CAM1, INCAM-100, CD antigen 106, cluster of differentiation 106, and CD106.

In certain aspects, the methods described herein are used to measure and/or detect VCAM-1. In certain aspects, the concentration or level of VCAM-1 is measured. In certain aspects, the biological sample in which VCAM-1 is measured is whole blood.

In certain aspects, the concentration of VCAM-1 is about 100 ng/mL to about 1500 ng/mL. In certain aspect, the concentration of VCAM-1 is about 100 ng/mL, 110 ng/mL, 120 ng/mL, 130 ng/mL, 140 ng/mL, 150 ng/mL, 160 ng/mL, 170 ng/mL, 180 ng/mL, 190 ng/mL, 200 ng/mL, 210 ng/mL, 220 ng/mL, 230 ng/mL, 240 ng/mL, 250 ng/mL, 260 ng/mL, 270 ng/mL, 280 ng/mL, 290 ng/mL, 300 ng/mL, 310 ng/mL, 320 ng/mL, 330 ng/mL, 340 ng/mL, 350 ng/mL, 360 ng/mL, 370 ng/mL, 380 ng/mL, 390 ng/mL, 400 ng/mL, 410 ng/mL, 420 ng/mL, 430 ng/mL, 440 ng/mL, 450 ng/mL, 460 ng/mL, 470 ng/mL, 480 ng/mL, 490 ng/mL, 500 ng/mL, 510 ng/mL, 520 ng/mL, 530 ng/mL, 540 ng/mL, 550 ng/mL, 560 ng/mL, 570 ng/mL, 580 ng/mL, 590 ng/mL, 600 ng/mL, 610 ng/mL, 620 ng/mL, 630 ng/mL, 640 ng/mL, 650 ng/mL, 660 ng/mL, 670 ng/mL, 680 ng/mL, 690 ng/mL, 700 ng/mL, 710 ng/mL, 720 ng/mL, 730 ng/mL, 740 ng/mL, 750 ng/mL, 760 ng/mL, 770 ng/mL, 780 ng/mL, 790 ng/mL, 800 ng/mL, 810 ng/mL, 820 ng/mL, 830 ng/mL, 840 ng/mL, 850 ng/mL, 860 ng/mL, 870 ng/mL, 880 ng/mL, 890 ng/mL, 900 ng/mL, 910 ng/mL, 920 ng/mL, 930 ng/mL, 940 ng/mL, 950 ng/mL, 960 ng/mL, 970 ng/mL, 980 ng/mL, 990 ng/mL, 1000 ng/mL, 1010 ng/mL, 1020 ng/mL, 1030 ng/mL, 1040 ng/mL, 1050 ng/mL, 1060 ng/mL, 1070 ng/mL, 1080 ng/mL, 1090 ng/mL, 1100 ng/mL, 1110 ng/mL, 1120 ng/mL, 1130 ng/mL, 1140 ng/mL, 1150 ng/mL, 1160 ng/mL, 1170 ng/mL, 1180 ng/mL, 1190 ng/mL, 1200 ng/mL, 1210 ng/mL, 1220 ng/mL, 1230 ng/mL, 1240 ng/mL, 1250 ng/mL, 1260 ng/mL, 1270 ng/mL, 1280 ng/mL, 1290 ng/mL, 1300 ng/mL, 1310 ng/mL, 1320 ng/mL, 1330 ng/mL, 1340 ng/mL, 1350 ng/mL, 1360 ng/mL, 1370 ng/mL, 1380 ng/mL, 1390 ng/mL, 1400 ng/mL, 1410 ng/mL, 1420 ng/mL, 1430 ng/mL, 1440 ng/mL, 1450 ng/mL, 1460 ng/mL, 1470 ng/mL, 1480 ng/mL, 1490 ng/mL, or 1500 ng/mL.

In certain aspects, the normal control concentration of VCAM-1 or reference value is about 100 to about 500 ng/mL. In certain aspect, the amount of VCAM-1 is about 100 ng/mL, 110 ng/mL, 120 ng/mL, 130 ng/mL, 140 ng/mL, 150 ng/mL, 160 ng/mL, 170 ng/mL, 180 ng/mL, 190 ng/mL, 200 ng/mL, 210 ng/mL, 220 ng/mL, 230 ng/mL, 240 ng/mL, 250 ng/mL, 260 ng/mL, 270 ng/mL, 280 ng/mL, 290 ng/mL, 300 ng/mL, 310 ng/mL, 320 ng/mL, 330 ng/mL, 340 ng/mL, 350 ng/mL, 360 ng/mL, 370 ng/mL, 380 ng/mL, 390 ng/mL, 400 ng/mL, 410 ng/mL, 420 ng/mL, 430 ng/mL, 440 ng/mL, 450 ng/mL, 460 ng/mL, 470 ng/mL, 480 ng/mL, 490 ng/mL, or 500 ng/mL.

In certain aspects, the concentration of VCAM-1 in the biological sample is deemed elevated when it is at least 10% to about 60% greater than the normal control concentration of VCAM-1. In certain aspects, the concentration of VCAM-1 in the biological sample is deemed elevated when it is at least about 10%, 15%, 20%, 25%, 30%, 35%, 40%, 45%, 50%, 55%, and/or 60% greater than the normal control concentration of VCAM-1. In certain aspects, the concentration of VCAM-1 in the biological sample is deemed elevated when it is at least 550 ng/mL (e.g., at least 560 ng/mL, 570 ng/mL, 580 ng/mL, 590 ng/mL, 600 ng/mL, 610 ng/mL, 620 ng/mL, 630 ng/mL, 640 ng/mL, 650 ng/mL, 660 ng/mL, 670 ng/mL, 680 ng/mL, 690 ng/mL, 700 ng/mL, 710 ng/mL, 720 ng/mL, 730 ng/mL, 740 ng/mL, 750 ng/mL, 760 ng/mL, 770 ng/mL, 780 ng/mL, 790 ng/mL, 800 ng/mL, 810 ng/mL, 820 ng/mL, 830 ng/mL, 840 ng/mL, 850 ng/mL, 860 ng/mL, 870 ng/mL, 880 ng/mL, 890 ng/mL, 900 ng/mL, 910 ng/mL, 920 ng/mL, 930 ng/mL, 940 ng/mL, 950 ng/mL, 960 ng/mL, 970 ng/mL, 980 ng/mL, 990 ng/mL, 1000 ng/mL, 1010 ng/mL, 1020 ng/mL, 1030 ng/mL, 1040 ng/mL, 1050 ng/mL, 1060 ng/mL, 1070 ng/mL, 1080 ng/mL, 1090 ng/mL, 1100 ng/mL, 1110 ng/mL, 1120 ng/mL, 1130 ng/mL, 1140 ng/mL, 1150 ng/mL, 1160 ng/mL, 1170 ng/mL, 1180 ng/mL, 1190 ng/mL, 1200 ng/mL, 1210 ng/mL, 1220 ng/mL, 1230 ng/mL, 1240 ng/mL, 1250 ng/mL, 1260 ng/mL, 1270 ng/mL, 1280 ng/mL, 1290 ng/mL, 1300 ng/mL, 1310 ng/mL, 1320 ng/mL, 1330 ng/mL, 1340 ng/mL, 1350 ng/mL, 1360 ng/mL, 1370 ng/mL, 1380 ng/mL, 1390 ng/mL, 1400 ng/mL, 1410 ng/mL, 1420 ng/mL, 1430 ng/mL, 1440 ng/mL, 1450 ng/mL, 1460 ng/mL, 1470 ng/mL, 1480 ng/mL, 1490 ng/mL, or 1500 ng/mL).

In some embodiments, the concentration of VCAM-1 in the biological sample is deemed elevated when it is at least 650 ng/mL (e.g., at least 660 ng/mL, 670 ng/mL, 680 ng/mL, 690 ng/mL, 700 ng/mL, 710 ng/mL, 720 ng/mL, 730 ng/mL, 740 ng/mL, 750 ng/mL, 760 ng/mL, 770 ng/mL, 780 ng/mL, 790 ng/mL, 800 ng/mL, 810 ng/mL, 820 ng/mL, 830 ng/mL, 840 ng/mL, 850 ng/mL, 860 ng/mL, 870 ng/mL, 880 ng/mL, 890 ng/mL, 900 ng/mL, 910 ng/mL, 920 ng/mL, 930 ng/mL, 940 ng/mL, 950 ng/mL, 960 ng/mL, 970 ng/mL, 980 ng/mL, 990 ng/mL, 1000 ng/mL, 1010 ng/mL, 1020 ng/mL, 1030 ng/mL, 1040 ng/mL, 1050 ng/mL, 1060 ng/mL, 1070 ng/mL, 1080 ng/mL, 1090 ng/mL, 1100 ng/mL, 1110 ng/mL, 1120 ng/mL, 1130 ng/mL, 1140 ng/mL, 1150 ng/mL, 1160 ng/mL, 1170 ng/mL, 1180 ng/mL, 1190 ng/mL, 1200 ng/mL, 1210 ng/mL, 1220 ng/mL, 1230 ng/mL, 1240 ng/mL, 1250 ng/mL, 1260 ng/mL, 1270 ng/mL, 1280 ng/mL, 1290 ng/mL, 1300 ng/mL, 1310 ng/mL, 1320 ng/mL, 1330 ng/mL, 1340 ng/mL, 1350 ng/mL, 1360 ng/mL, 1370 ng/mL, 1380 ng/mL, 1390 ng/mL, 1400 ng/mL, 1410 ng/mL, 1420 ng/mL, 1430 ng/mL, 1440 ng/mL, 1450 ng/mL, 1460 ng/mL, 1470 ng/mL, 1480 ng/mL, 1490 ng/mL, or 1500 ng/mL).

In some embodiments, the concentration of VCAM-1 in the biological sample is elevated when it is 650 ng/mL to 1500 ng/mL (e.g., 650 ng/mL to 1400 ng/mL, 650 ng/mL to 1300 ng/mL, 650 ng/mL to 1200 ng/mL, 650 ng/mL to 1100 ng/mL, 650 ng/mL to 1000 ng/mL, 650 ng/mL to 900 ng/mL, 650 ng/mL to 800 ng/mL, 650 ng/mL to 700 ng/mL, 700 ng/mL to 1500 ng/mL, 800 ng/mL to 1500 ng/mL, 900 ng/mL to 1500 ng/mL, 1000 ng/mL to 1500 ng/mL, 1100 ng/mL to 1500 ng/mL, 1200 ng/mL to 1500 ng/mL, 1300 ng/mL to 1500 ng/mL, or 1400 ng/mL to 1500 ng/mL).

In certain aspects, the methods herein can be used to discriminate between nonalcoholic fatty liver (NAFL) and nonalcoholic steatohepatitis (NASH), by measuring a quantity of VCAM-1 contained in blood collected from a subject; and determining that the subject is affected with or possibly affected with NASH in a case that the quantity of VCAM-1 is elevated or larger than a reference value.

In certain aspects, the methods herein can be used to determine the presence of fibrosis such as hepatic fibrosis by measuring a quantity of VCAM-1 contained in blood collected from a subject; and determining that the subject has or possibly has a symptom of hepatic fibrosis in a case that the quantity of VCAM-1 is elevated or larger than a reference value.

In certain aspects, the method herein can be used to determine a degree of progression of a symptom of nonalcoholic fatty liver disease (NAFLD), by measuring a quantity of VCAM-1 contained in blood collected from a subject as the quantity of VCAM-1 is larger than a reference value.

In certain aspects, the methods herein can be used to determine the degree of progression of a symptom of NAFLD, NAFL or NASH by monitoring the level of VCAM-1.

IV. Alpha-2-Macroglobulin (A2M)

A2M is a plasma protein found in the blood that mainly acts as an antiprotease and is able to inactivate a variety of proteinases. For example, it functions as an inhibitor of fibrinolysis by inhibiting plasmin and kallikrein. It functions as an inhibitor of coagulation by inhibiting thrombin. Further, A2M sometimes acts as a carrier protein because it also binds to numerous growth factors and cytokines, such as platelet-derived growth factor, basic fibroblast growth factor, TGF-β, insulin, and IL-1β. A2M is mainly produced by the liver, and also locally synthesized by macrophages, fibroblasts, and adrenocortical cells. In humans it is encoded by the A2M gene. A2M HUMAN, accession P01023, is SEQ ID NO: 2. A2M has 1474 amino acids and a mass of approximately 720 kDa. The human A2M mRNA (coding) sequence is set forth in, e.g., Genbank Accession No. NM_000014.5. One skilled in the art will appreciate that A2M is also known as A2MD, CPAMD5, FWP007, S863-7, or transcuprein.

In certain aspects, the methods described herein are used to measure and/or detect A2M. In certain aspects, the concentration or level of A2M is measured. In certain aspects, the biological sample in which A2M is measured is whole blood.

In certain aspects, the concentration of A2M is about 0.1 mg/mL to about 10 mg/mL. In some embodiments, the concentration of A2M is about 0.09 mg/mL, 0.1 mg/mL, 0.11 mg/mL, 0.12 mg/mL, 0.14 mg/mL, 0.16 mg/mL, 0.18 mg/mL, 0.2 mg/mL, 0.4 mg/mL, 0.6 mg/mL, 0.8 mg/mL, 1 mg/mL, 1.2 mg/mL, 1.4 mg/mL, 1.6 mg/mL, 1.8 mg/mL, 2 mg/mL, 2.2 mg/mL, 2.4 mg/mL, 2.6 mg/mL, 2.8 mg/mL, 3 mg/mL, 3.2 mg/mL, 3.4 mg/mL, 3.6 mg/mL, 3.8 mg/mL, 4 mg/mL, 4.2 mg/mL, 4.4 mg/mL, 4.6 mg/mL, 4.8 mg/mL, 5 mg/mL, 5.2 mg/mL, 5.4 mg/mL, 5.6 mg/mL, 5.8 mg/mL, 6 mg/mL, 6.2 mg/mL, 6.4 mg/mL, 6.6 mg/mL, 6.8 mg/mL, 7 mg/mL, 7.2 mg/mL, 7.4 mg/mL, 7.6 mg/mL, 7.8 mg/mL, 8 mg/mL, 8.2 mg/mL, 8.4 mg/mL, 8.6 mg/mL, 8.8 mg/mL, 9 mg/mL, 9.2 mg/mL, 9.4 mg/mL, 9.6 mg/mL, 9.8 mg/mL, or 10 mg/mL.

In certain aspects, the normal control concentration of A2M or reference value is about 1 mg/mL to about 5 mg/mL. In some embodiments, the normal control concentration of A2M is about 0.9 mg/mL, 1 mg/mL, 1.1 mg/mL, 1.2 mg/mL, 1.4 mg/mL, 1.6 mg/mL, 1.8 mg/mL, 2 mg/mL, 2.2 mg/mL, 2.4 mg/mL, 2.6 mg/mL, 2.8 mg/mL, 3 mg/mL, 3.2 mg/mL, 3.4 mg/mL, 3.6 mg/mL, 3.8 mg/mL, 4 mg/mL, 4.2 mg/mL, 4.4 mg/mL, 4.6 mg/mL, 4.8 mg/mL, or 5 mg/mL.

In certain aspects, the concentration of A2M in the biological sample is deemed elevated when it is at least 10% to about 60% greater than the normal control concentration of A2M. In certain aspects, the concentration of A2M in the biological sample is deemed elevated when it is at least about 10%, 15%, 20%, 25%, 30%, 35%, 40%, 45%, 50%, 55%, and/or 60% greater than the normal control concentration of A2M. In certain aspects, the concentration of A2M in the biological sample is deemed elevated when it is at least 5.5 mg/mL (e.g., a least 5.6 mg/mL, 5.7 mg/mL, 5.8 mg/mL, 5.9 mg/mL, 6 mg/mL, 6.5 mg/mL, 7 mg/mL, 7.5 mg/mL, 8 mg/mL, 8.5 mg/mL, 9 mg/mL, 9.5 mg/mL, or 10 mg/mL). In some embodiments, the concentration of A2M in the biological sample is deemed elevated when it is at least 6.5 mg/mL (e.g., a least 6.6 mg/mL, 6.7 mg/mL, 6.8 mg/mL, 6.9 mg/mL, 7 mg/mL, 7.5 mg/mL, 8 mg/mL, 8.5 mg/mL, 9 mg/mL, 9.5 mg/mL, or 10 mg/mL).

In certain aspects, the methods herein can be used to discriminate between nonalcoholic fatty liver (NAFL) and nonalcoholic steatohepatitis (NASH), by measuring a quantity of A2M contained in blood collected from a subject; and determining that the subject is affected with or possibly affected with NASH in a case that the quantity of A2M is elevated or larger than a reference value.

In certain aspects, the methods herein can be used to determine the presence of fibrosis such as hepatic fibrosis by measuring a quantity of A2M contained in blood collected from a subject; and determining that the subject has or possibly has a symptom of hepatic fibrosis in a case that the quantity of A2M is elevated or larger than a reference value.

In certain aspects, the method herein can be used to determine a degree of progression of a symptom of nonalcoholic fatty liver disease (NAFLD), by measuring a quantity of A2M contained in blood collected from a subject as the quantity of A2M is larger than a reference value.

In certain aspects, the methods herein can be used to determine the degree of progression of a symptom of NAFLD, NAFL or NASH by monitoring the level of A2M.

V. Device

Various instruments and devices are suitable for use in the present disclosure. Many spectrophotometers have the capability to measure fluorescence. Fluorescence is the molecular absorption of light energy at one wavelength and its nearly instantaneous re-emission at another, longer wavelength. Some molecules fluoresce naturally, and others must be modified to fluoresce.

A fluorescence spectrophotometer or fluorometer, fluorospectrometer, or fluorescence spectrometer measures the fluorescent light emitted from a sample at different wavelengths, after illumination with light source such as a xenon flash lamp. Fluorometers can have different channels for measuring differently-colored fluorescent signals (that differ in their wavelengths), such as green and blue, or ultraviolet and blue, channels. In one aspect, a suitable device includes an ability to perform a time-resolved fluorescence resonance energy transfer (FRET) experiment.

Suitable fluorometers can hold samples in different ways, including cuvettes, capillaries, Petri dishes, and microplates. The assays described herein can be performed on any of these types of instruments. In certain aspects, the device has an optional microplate reader, allowing emission scans in up to 384-well plates. Others models suitable for use hold the sample in place using surface tension.

Time-resolved fluorescence (TRF) measurement is similar to fluorescence intensity measurement. One difference, however, is the timing of the excitation/measurement process. When measuring fluorescence intensity, the excitation and emission processes are simultaneous: the light emitted by the sample is measured while excitation is taking place. Even though emission systems are very efficient at removing excitation light before it reaches the detector, the amount of excitation light compared to emission light is such that fluorescent intensity measurements exhibit elevated background signals. The present disclosure offers a solution to this issue. Time resolve FRET relies on the use of specific fluorescent molecules that have the property of emitting over long periods of time (measured in milliseconds) after excitation, when most standard fluorescent dyes (e.g., fluorescein) emit within a few nanoseconds of being excited. As a result, it is possible to excite cryptate lanthanides using a pulsed light source (e.g., Xenon flash lamp or pulsed laser), and measure after the excitation pulse.

As the donor and acceptor fluorescent compounds attached to the antibodies move closer together, an energy transfer is caused from the donor compound to the acceptor compound, resulting in a decrease in the fluorescence signal emitted by the donor compound and an increase in the signal emitted by the acceptor compound, and vice-versa. The majority of biological phenomena involving interactions between different partners will therefore be able to be studied by measuring the change in FRET between two fluorescent compounds coupled with compounds which will be at a greater or lesser distance, depending on the biological phenomenon in question.

The FRET signal can be measured in different ways: measurement of the fluorescence emitted by the donor alone, by the acceptor alone or by the donor and the acceptor, or measurement of the variation in the polarization of the light emitted in the medium by the acceptor as a result of FRET. One can also include measurement of FRET by observing the variation in the lifetime of the donor, which is facilitated by using a donor with a long fluorescence lifetime, such as rare earth complexes (especially on simple equipment like plate readers). Furthermore, the FRET signal can be measured at a precise instant or at regular intervals, making it possible to study its change over time and thereby to investigate the kinetics of the biological process studied.

In certain aspects, the device disclosed in PCT/IB2019/051213, filed Feb. 14, 2019 is used, which is hereby incorporated by reference. That disclosure in that application generally relates to analyzers that can be used in point-of-care settings to measure the absorbance and fluorescence of a sample with minimal or no user handling or interaction. The disclosed analyzers provide advantageous features of more rapid and reliable analyses of samples having properties that can be detected with each of these two approaches. For example, it can be beneficial to quantify both the fluorescence and absorbance of a blood sample being subjected to a diagnostic assay. In some analytical workflows, the hematocrit of a blood sample can be quantified with an absorbance assay, while the signal intensities measured in a FRET assay can provide information regarding other components of the blood sample.

One apparatus disclosed in PCT/IB2019/051213 is useful for detecting an emission light from a sample, and absorbance of a transillumination light by the sample, which comprises a first light source configured to emit an excitation light having an excitation wavelength. The apparatus further comprises a second light source configured to transilluminate the sample with the transillumination light. The apparatus further comprises a first light detector configured to detect the excitation light, and a second light detector configured to detect the emission light and the transillumination light. The apparatus further comprises a dichroic mirror configured to (1) epi-illuminate the sample by reflecting at least a portion of the excitation light, (2) transmit at least a portion of the excitation light to the first light detector, (3) transmit at least a portion of the emission light to the second light detector, and (4) transmit at least a portion of the transillumination light to the second light detector.

One suitable cuvette for use in the present disclosure is disclosed in PCT/IB2019/051215, filed Feb. 14, 2019. One of the provided cuvettes comprises a hollow body enclosing an inner chamber having an open chamber top. The cuvette further comprises a lower lid having an inner wall, an outer wall, an open lid top, and an open lid bottom. At least a portion of the lower lid is configured to fit inside the inner chamber proximate to the open chamber top. The lower lid comprises one or more (e.g., two or more) containers connected to the inner wall, wherein each of the containers has an open container top. In certain aspects, the lower lid comprises two or more such containers. The lower lid further comprises a securing means connected to the hollow body. The cuvette further comprises an upper lid wherein at least a portion of the upper lid is configured to fit inside the lower lid proximate to the open lid top.

VI. Example

This example illustrates a method of this disclosure for detecting the presence and amounts of VCAM-1 and A2M in a TR-FRET assay. As shown in FIG. 1, VCAM-1 binds to an anti-VCAM-1 antibody (MAB-1) labeled with a donor fluorophore and a second anti-VCAM-1 antibody (MAB-2) labeled with an acceptor fluorophore (NIR acceptor). An isolated A2M protein labeled with an acceptor fluorophore (Green acceptor) binds to an anti-A2M antibody (MAB) labeled with a donor fluorophore. The VCAM-1 analyte is in a sample from a patient (i.e., whole blood sample) and it binds to both anti-VCAM-1 antibodies simultaneously resulting in a FRET signal. The A2M analyte in a sample from a patient (i.e., whole blood sample) competes with the isolated A2M protein for binding to the anti-A2M antibody, thus, disrupting the FRET signal from the anti-A2M antibody labeled with the donor fluorophore and the isolated A2M protein labeled with the acceptor fluorophore.

Figure 2A:
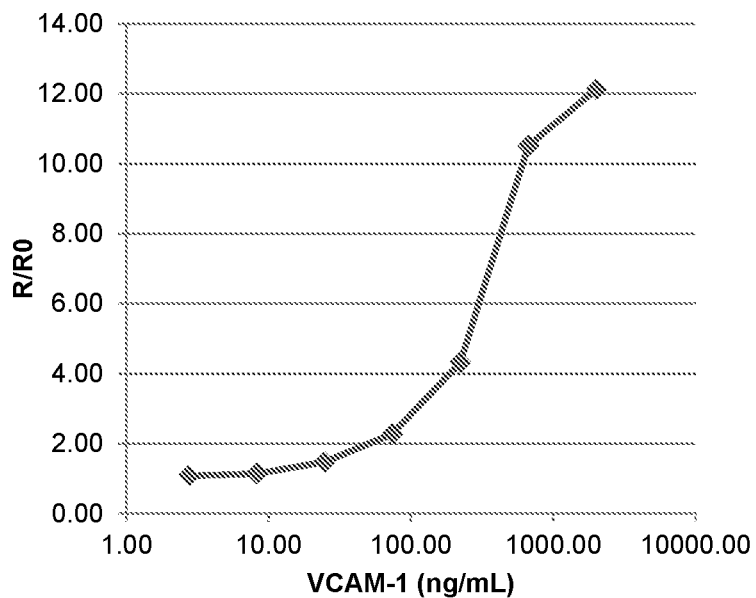
FIGS. 2A-2D illustrate standard curves generated for VCAM-1 using methods of the present disclosure.
Figure 2B:
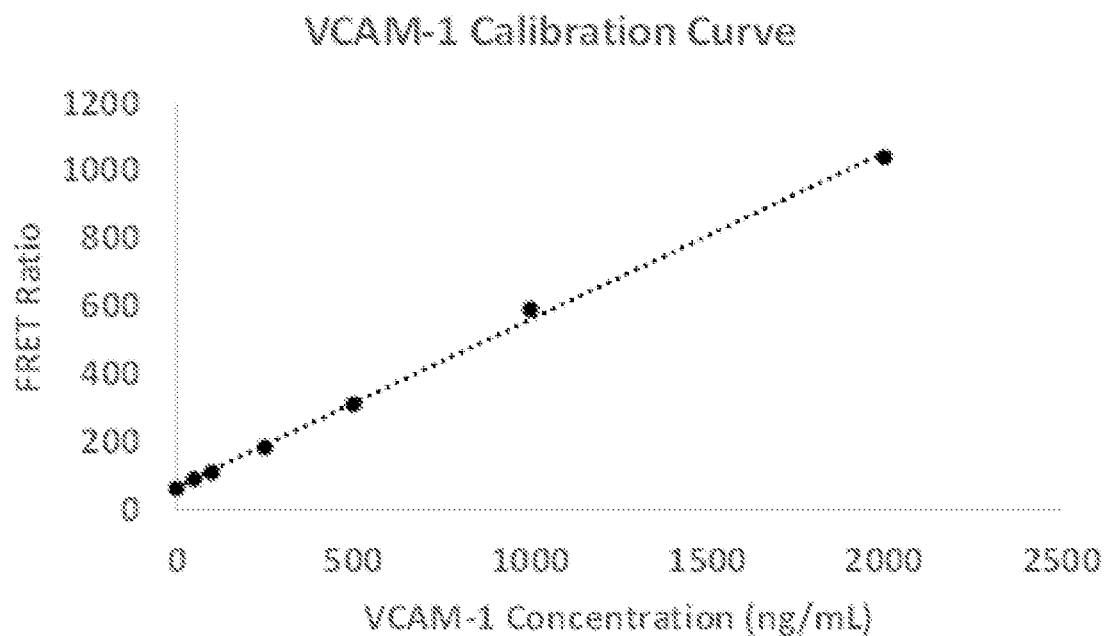
Figure 2C:
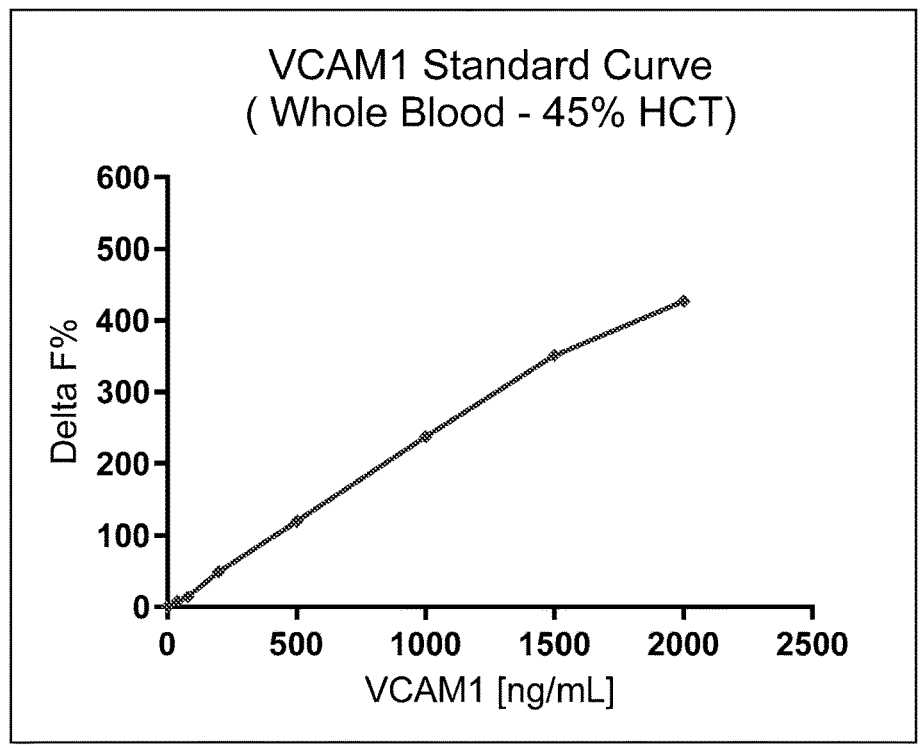
Figure 2D:
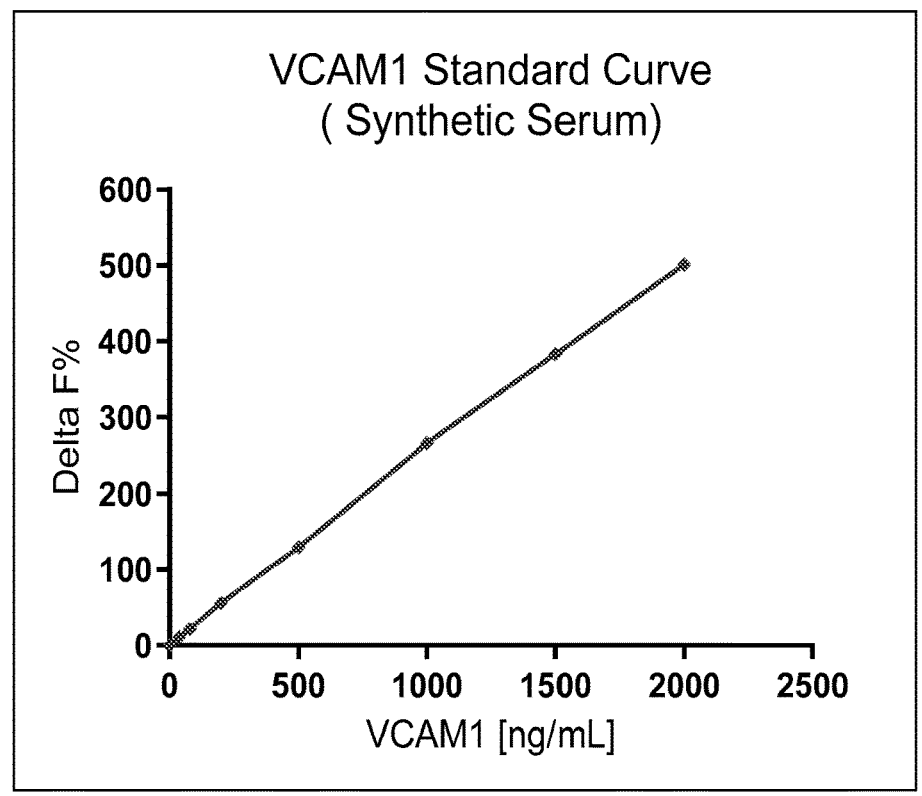
Figure 2E:
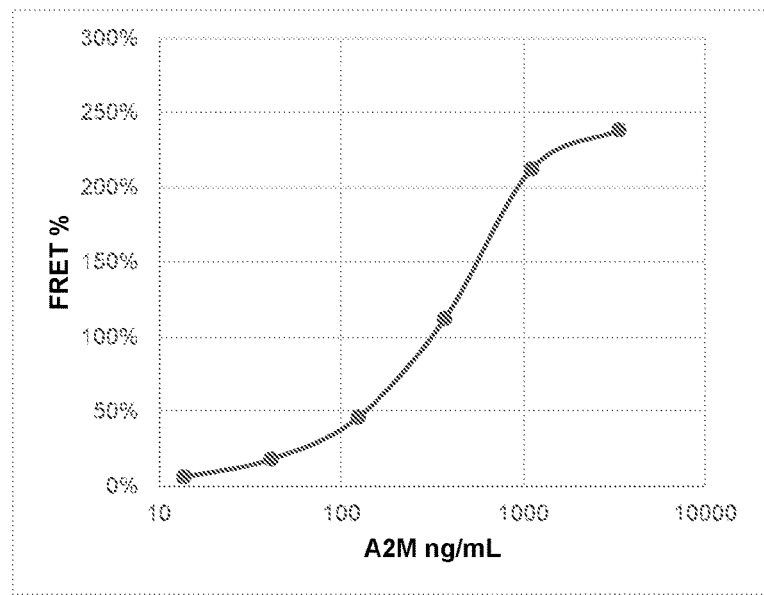
FIGS. 2E-2G illustrate standard curves generated for A2M using methods of the present disclosure.
Figure 2F:
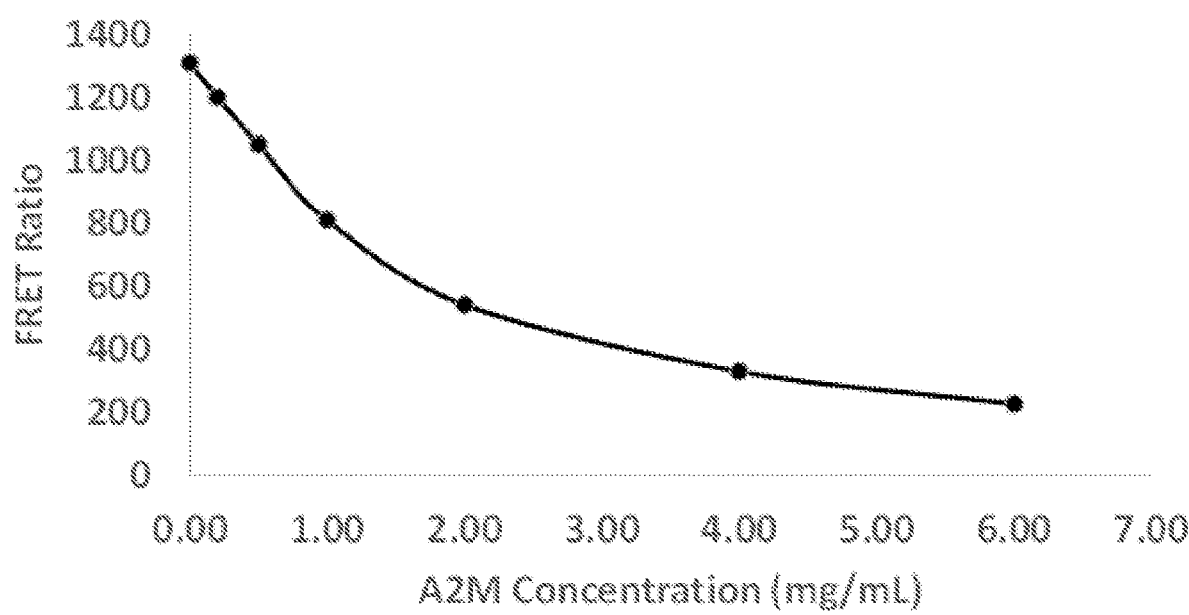
Figure 2G:
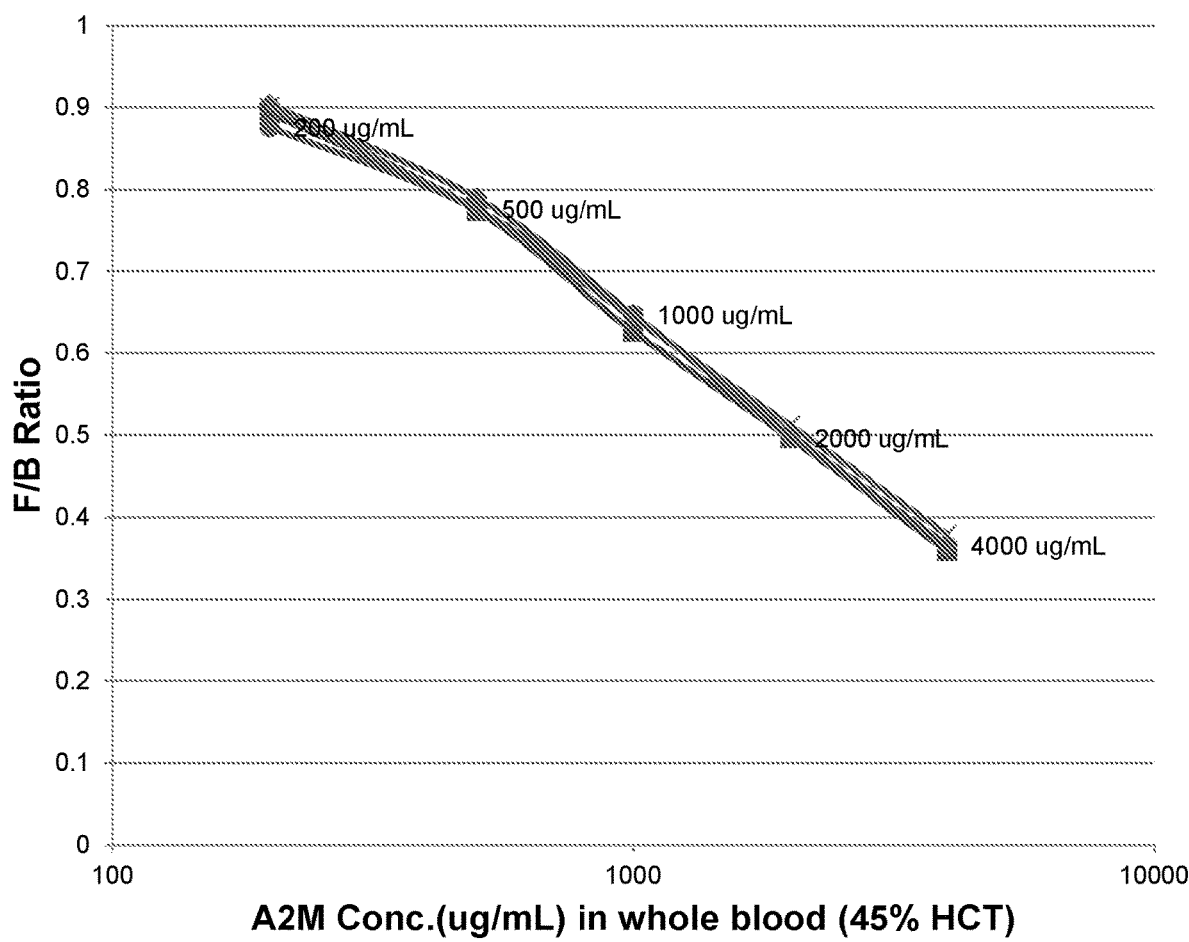

If one anti-VCAM-1 antibody is labeled with a donor fluorophore and a second anti-VCAM-1 antibody is labeled with an acceptor fluorophore, and an anti-A2M antibody is labeled with a donor fluorophore and an isolated A2M protein is labeled with an acceptor fluorophore, in which the two acceptor fluorophores are different, TR-FRET can occur in the presence of the VCAM-1 and the FRET signal would disappear in the presence of the A2M in the sample (FIG. 1). The increase in FRET signal of the acceptor fluorophore on the anti-VCAM-1 antibody is proportional to the level of VCAM-1 present in the patient's blood as interpolated from a known amount of VCAM-1 calibrator (FIGS. 2A-2D). Table 1 below shows the corresponding numerical data for FIG. 2C and Table 2 below shows the corresponding numerical data for FIG. 2D. The FRET signal of the acceptor fluorophore on the anti-A2M antibody or the isolated A2M protein is inversely proportional to the level of A2M present in the patient's blood as interpolated from a known amount of A2M calibrator (FIGS. 2E-2G). Table 3 below shows the corresponding average numerical data for FIG. 2G, which includes 4 replicates.

TABLE 1

| STDS [ng/mL] | Delta F % |
| --- | --- |
| 2000 | 427 |
| 1500 | 351 |
| 1000 | 237 |
| 500 | 119 |
| 200 | 49 |
| 80 | 14 |
| 40 | 8 |
| 0 | 0 |

TABLE 2

| STDS [ng/mL] | Delta F % |
| --- | --- |
| 2000 | 501 |
| 1500 | 383 |
| 1000 | 266 |
| 500 | 129 |
| 200 | 56 |
| 80 | 22 |
| 40 | 11 |
| 0 | 0 |

TABLE 3

| Conc.(ug/mL) | F/B Mean | F/B Std | % CV |
| --- | --- | --- | --- |
| 4000 | 0.393 | 0.009 | 2.17% |
| 2000 | 0.532 | 0.007 | 1.36% |
| 1000 | 0.666 | 0.010 | 1.47% |
| 500 | 0.795 | 0.007 | 0.93% |
| 200 | 0.905 | 0.013 | 1.39% |
| 0 | 1.000 | 0.000 | 0.00% |

Figure 2H:
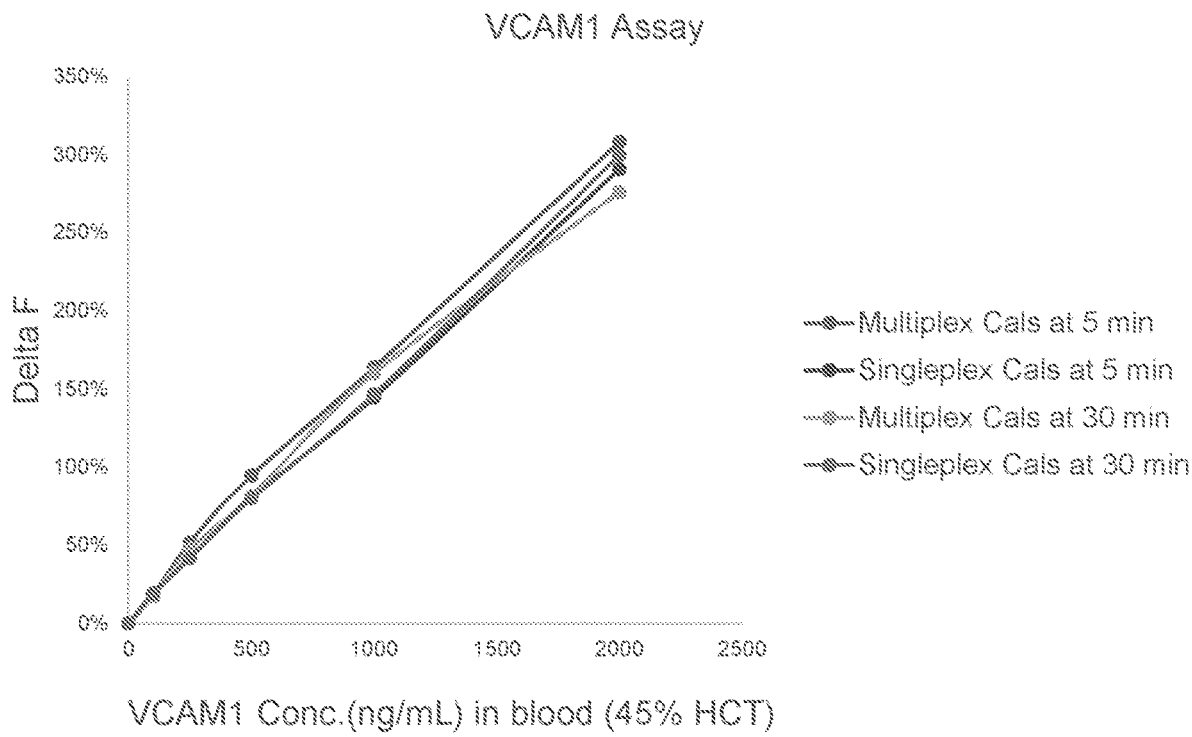
FIGS. 2H and 2I illustrate standard curves generated for VCAM-1 and A2M during a multiplex assay using methods of the present disclosure.
Figure 2I:
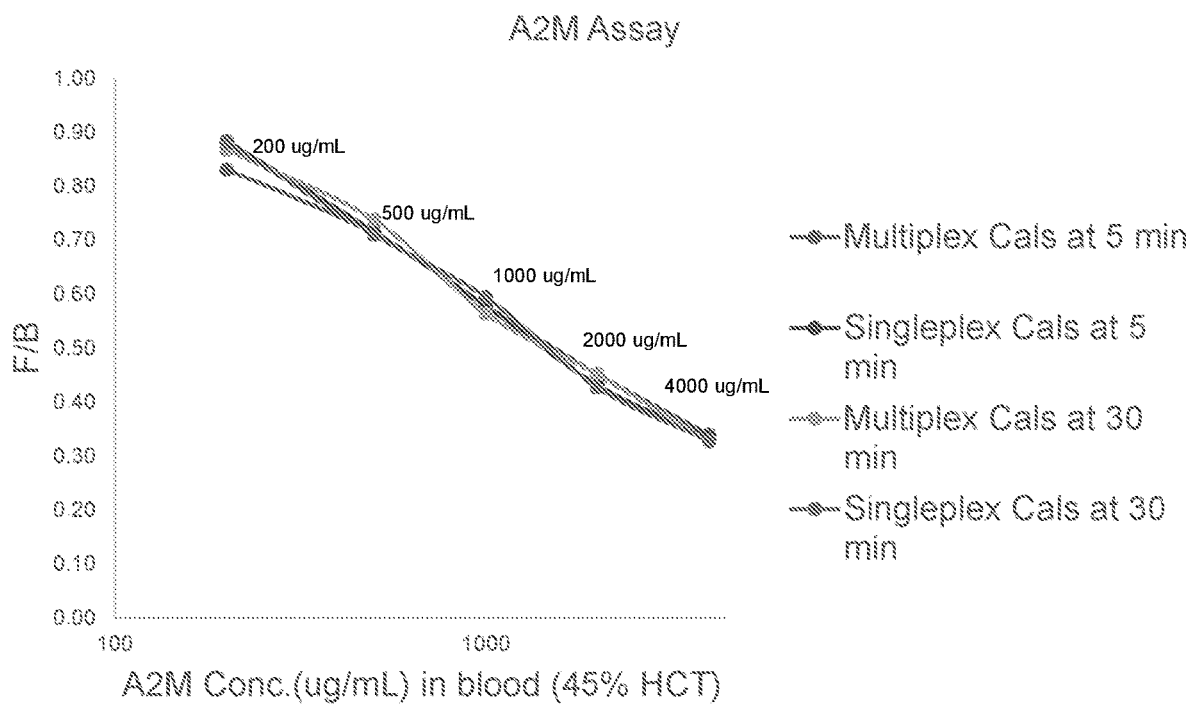

A multiplex assay was also performed to generate standard curves for VCAM-1 and A2M simultaneously in whole blood (FIGS. 2H and 2I). Three separate calibration curves were prepared: 1) VCAM-1 only 2) A2M only 3) VCAM-1 and A2M combined. The concentration of both VCAM-1 and A2M were held constant between the individual calibration curves and the combined curve. All three calibration curves were tested at 5 and 30 minutes. Table 4 below shows the corresponding numerical data for FIG. 2H and Table 5 below shows the corresponding numerical data for FIG. 2I.

TABLE 4

| VCAM-1 (ng/mL) | Multiplex Cals at 5 mins | Singleplex Cals at 5 mins | Multiplex Cals at 30 mins | Singleplex Cals at 30 mins |
| --- | --- | --- | --- | --- |
| 2000 | 308% | 291% | 276% | 300% |
| 1000 | 164% | 145% | 160% | 147% |
| 500 | 95% | 81% | 81% | 80% |
| 250 | 51% | 41% | 47% | 42% |
| 100 | 18% | 19% | 17% | 19% |
| 0 | 0% | 0% | 0% | 0% |

TABLE 5

| A2M (µg/mL) | Multiplex Cals at 5 mins | Singleplex Cals at 5 mins | Multiplex Cals at 30 mins | Singleplex Cals at 30 mins |
| --- | --- | --- | --- | --- |
| 4000 | 0.34 | 0.33 | 0.33 | 0.33 |
| 2000 | 0.45 | 0.43 | 0.45 | 0.43 |
| 1000 | 0.58 | 0.58 | 0.56 | 0.59 |
| 500 | 0.71 | 0.72 | 0.74 | 0.71 |
| 200 | 0.83 | 0.88 | 0.87 | 0.88 |
| 0 | 1.00 | 1.00 | 1.00 | 1.00 |

Figure 2J:
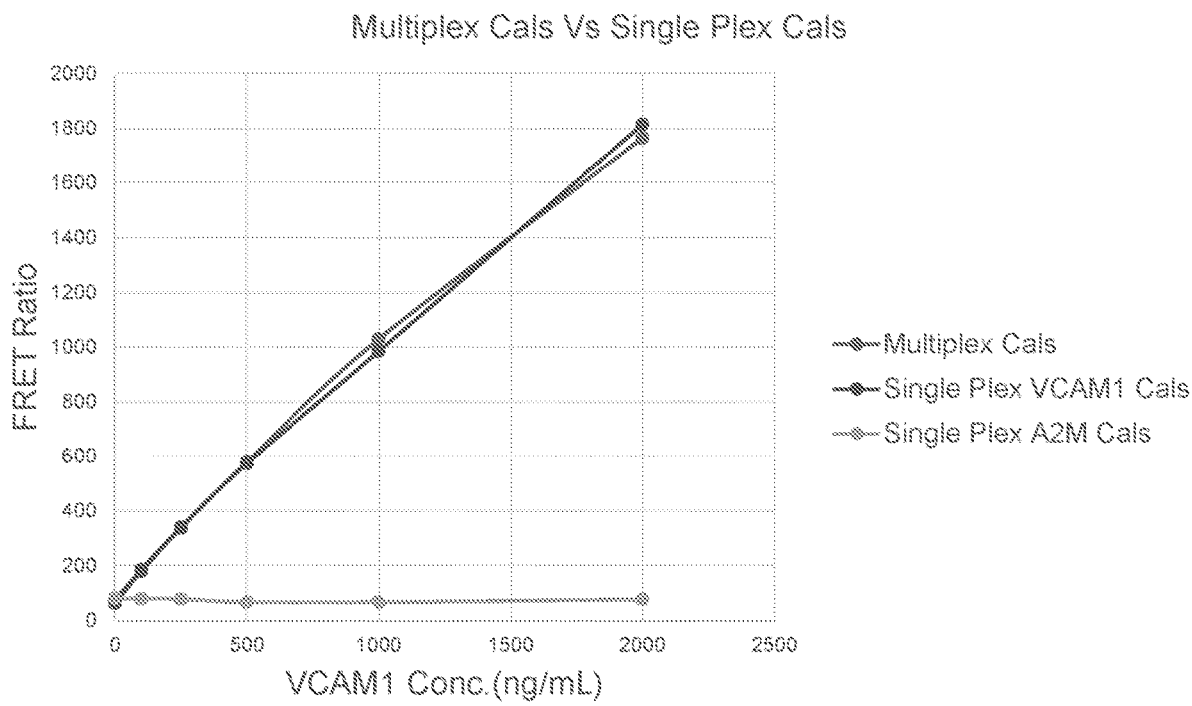
FIGS. 2J and 2K illustrate that when A2M and VCAM-1 are multiplexed, the results are comparable to the single plex assay.
Figure 2K:
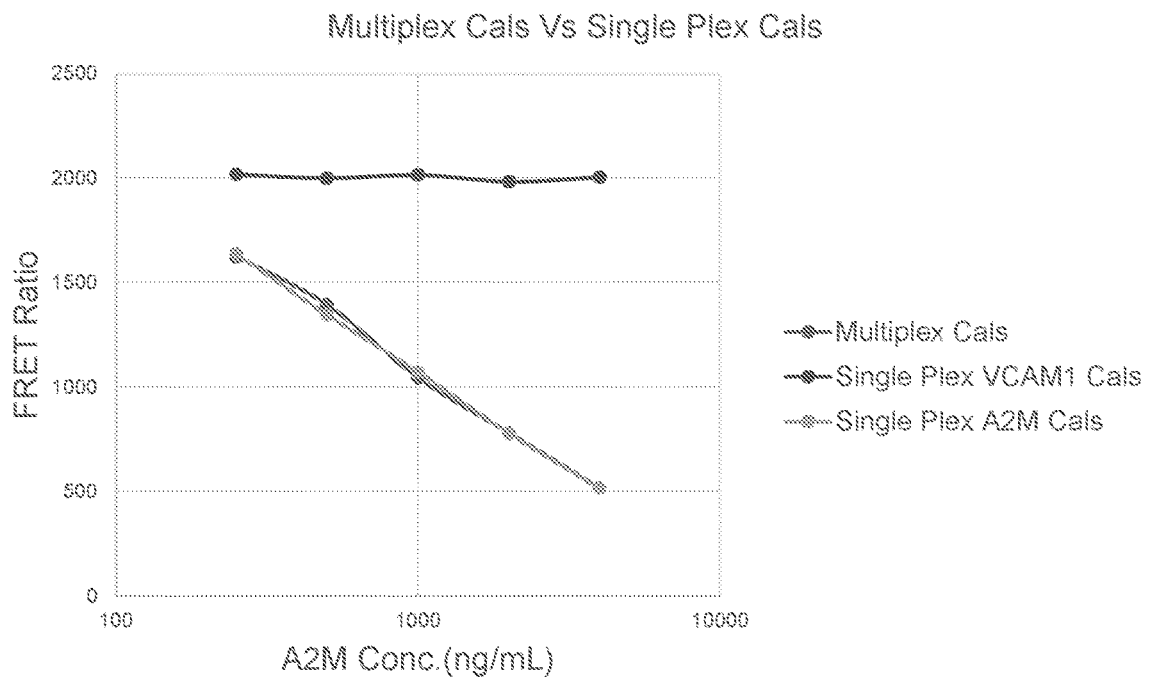

FIGS. 2J and 2K illustrate that when A2M and VCAM-1 are multiplexed, the results are comparable to the single plex assay. FIG. 2J shows that the multiplexed VCAM-1 results overlay with the single plex VCAM-1 results while A2M results do not show a dose response. Similarly, FIG. 2K shows that the multiplexed A2M results overlay with the single plex A2M results while VCAM-1 results do not show a dose response. Table 6 below shows the corresponding numerical data for FIGS. 2J and 2K.

TABLE 6

| ID | Targeted VCAM1 (ng/mL) | BackCalc. VCAM1 (ng/mL) | Recovery | Targeted A2M (ug/mL) | BackCalc. VCAM1 (ng/mL) | Recovery |
| --- | --- | --- | --- | --- | --- | --- |
| VCAM1 Cal 1 | 2000 | 2074.4 | 104% | 0 | N/A | N/A |
| VCAM1 Cal 2 | 1000 | 948.9 | 95% | 0 | NA | N/A |
| VCAM1 Cal 3 | 500 | 489.3 | 98% | 0 | 2.57 | N/A |
| VCAM1 Cal 4 | 250 | 246.9 | 99% | 0 | N/A | N/A |
| VCAM1 Cal 5 | 100 | 95.2 | 95% | 0 | N/A | N/A |
| VCAM1 Cal 6 | 0 | N/A | N/A | 0 | N/A | N/A |
| A2M Cal 1 | 0 | 1.3 | N/A | 4000 | 4076.5 | 102% |
| A2M Cal 2 | 0 | N/A | N/A | 2000 | 1947.2 | 97% |
| A2M Cal 3 | 0 | N/A | N/A | 1000 | 987.9 | 99% |
| A2M Cal 4 | 0 | 2.9 | N/A | 500 | 536.8 | 107% |
| A2M Cal 5 | 0 | 3.8 | N/A | 250 | 245.9 | 98% |
| A2M Cal 6 | 0 | 5.2 | N/A | 0 | N/A | N/A |

Donor fluorophore, Lumi4-Tb (also called Tb-H22TRENIAM-5LIO-NHS, FIG. 3), can be used to label an anti-VCAM-1 antibody, an anti-A2M antibody, or an isolated A2M protein. Lumi4-Tb has 3 spectrally distinct peaks, at 490, 550, and 620 nm, which can be used for energy transfer (FIG. 5). The acceptor fluorophores that can be used include but are not limited to: AlexaFluor 488, AlexaFluor 546, and AlexaFluor 647 (FIG. 5). Donor and acceptor fluorophores can be conjugated to antibodies using primary amines on antibodies.

The sequence of human VCAM-1 (accession P19320) is shown below:

SEQ ID NO: 1:
MPGKMVVILGASNILWIMFAASQAFKIETTPESRYLAQIGDSVSLTCST
TGCESPFFSWRTQIDSPLNGKVTNEGTTSTLTMNPVSFGNEHSYLCTAT
CESRKLEKGIQVEIYSFPKDPEIHLSGPLEAGKPITVKCSVADVYPFDR
LEIDLLKGDHLMKSQEFLEDADRKSLETKSLEVTFTPVIEDIGKVLVCR
AKLHIDEMDSVPTVRQAVKELQVYISPKNTVISVNPSTKLQEGGSVTMT
CSSEGLPAPEIFWSKKLDNGNLQHLSGNATLTLIAMRMEDSGIYVCEGV
NLIGKNRKEVELIVQEKPFTVEISPGPRIAAQIGDSVMLTCSVMGCESP
SFSWRTQIDSPLSGKVRSEGTNSTLTLSPVSFENEHSYLCTVTCGHKKL
EKGIQVELYSFPRDPEIEMSGGLVNGSSVTVSCKVPSVYPLDRLEIELL
KGETILENIEFLEDTDMKSLENKSLEMTFIPTIEDTGKALVCQAKLHID
DMEFEPKQRQSTQTLYVNVAPRDTTVLVSPSSILEEGSSVNMTCLSQGF
PAPKILWSRQLPNGELQPLSENATLTLISTKMEDSGVYLCEGINQAGRS
RKEVELIIQVTPKDIKLTAFPSESVKEGDTVIISCTCGNVPETWIILKK
KAETGDTVLKSIDGAYTIRKAQLKDAGVYECESKNKVGSQLRSLTLDVQ
GRENNKDYFSPELLVLYFASSLIIPAIGMIIYFARKANMKGSYSLVEAQ
KSKV

The sequence of human A2M (accession P01023) is shown below:

SEQ ID NO: 2:
MGKNKLLHPSLVLLLLVLLPTDASVSGKPQYMVLVPSLLHTETTEKGCV
LLSYLNETVTVSASLESVRGNRSLFTDLEAENDVLHCVAFAVPKSSSNE
EVMFLTVQVKGPTQEFKKRTTVMVKNEDSLVFVQTDKSIYKPGQTVKFR
VVSMDENFHPLNELIPLVYIQDPKGNRIAQWQSFQLEGGLKQFSFPLSS
EPFQGSYKVVVQKKSGGRTEHPFTVEEFVLPKFEVQVTVPKIITILEEE
MNVSVCGLYTYGKPVPGHVTVSICRKYSDASDCHGEDSQAFCEKFSGQL
NSHGCFYQQVKTKVFQLKRKEYEMKLHTEAQIQEEGTVVELTGRQSSEI
TRTITKLSFVKVDSHFRQGIPFFGQVRLVDGKGVPIPNKVIFIRGNEAN
YYSNATTDEHGLVQFSINTTNVMGTSLTVRVNYKDRSPCYGYQWVSEEH
EEAHHTAYLVFSPSKSFVHLEPMSHELPCGHTQTVQAHYILNGGTLLGL
KKLSFYYLIMAKGGIVRTGTHGLLVKQEDMKGHFSISIPVKSDIAPVAR
LLIYAVLPTGDVIGDSAKYDVENCLANKVDLSFSPSQSLPASHAHLRVT
AAPQSVCALRAVDQSVLLMKPDAELSASSVYNLLPEKDLTGFPGPLNDQ
DNEDCINRHNVYINGITYTPVSSTNEKDMYSFLEDMGLKAFTNSKIRKP
KMCPQLQQYEMHGPEGLRVGFYESDVMGRGHARLVHVEEPHTETVRKYF
PETWIWDLVVVNSAGVAEVGVTVPDTITEWKAGAFCLSEDAGLGISSTA
SLRAFQPFFVELTMPYSVIRGEAFTLKATVLNYLPKCIRVSVQLEASPA
FLAVPVEKEQAPHCICANGRQTVSWAVTPKSLGNVNFTVSAEALESQEL
CGTEVPSVPEHGRKDTVIKPLLVEPEGLEKETTFNSLLCPSGGEVSEEL
SLKLPPNVVEESARASVSVLGDILGSAMQNTQNLLQMPYGCGEQNMVLF
APNIYVLDYLNETQQLTPEIKSKAIGYLNTGYQRQLNYKHYDGSYSTFG
ERYGRNQGNTWLTAFVLKTFAQARAYIFIDEAHITQALIWLSQRQKDNG
CFRSSGSLLNNAIKGGVEDEVTLSAYITIALLEIPLTVTHPVVRNALFC
LESAWKTAQEGDHGSHVYTKALLAYAFALAGNQDKREVLKSLNEEAVK
KDNSVHWERPQKPKAPVGHFYEPQAPSAEVEMTSYVLLAYLTAQPAPTS
EDLTSATNIVKWITKQQNAQGGFSSTQDTVVALHALSKYGAATFTRTGK
AAQVTIQSSGTFSSKFQVDNNNRLLLQQVSLPELPGEYSMKVTGEGCVY
LQTSLKYNILPEKEEFPFALGVQTLPQTCDEPKAHTSFQISLSVSYTGS
RSASNMAIVDVKMVSGFIPLKPTVKMLERSNHVSRTEVSSNHVLIYLDK
VSNQTLSLFFTVLQDVPVRDLKPAIVKVYDYYETDEFAIAEYNAPCSKD
LGNA

What is claimed is:

1. A homogeneous assay method for detecting the presence or amount of vascular cell adhesion protein 1 (VCAM-1) using only a sandwich assay and alpha-2-macroglobulin (A2M) using only a competitive assay in a sample, the method comprising:

in the sandwich assay, contacting the sample with a first anti-VCAM-1 antibody, which binds to a first epitope of VCAM-1, wherein the first anti-VCAM-1 antibody is labeled with a first donor fluorophore;

contacting the sample with a second anti-VCAM-1 antibody, which binds to a second epitope of VCAM-1, wherein the second anti-VCAM-1 antibody is labeled with a first acceptor fluorophore;

in the competitive assay, contacting the sample with an anti-A2M antibody, which binds to an epitope of A2M, wherein the anti-A2M antibody is labeled with a second donor fluorophore;

contacting the sample with an isolated A2M protein, wherein the isolated A2M protein is labeled with a second acceptor fluorophore;

incubating the sample for a time sufficient to obtain dual antibody labeled VCAM-1 and antibody labeled A2M; and exciting the sample having dual antibody labeled VCAM-1 and antibody labeled A2M using one or more light sources to detect a single fluorescence emission signal associated with fluorescence resonance energy transfer (FRET) for the first acceptor fluorophore and a single fluorescence emission signal associated with FRET for the second acceptor fluorophore, wherein the first and second acceptor fluorophores are different.

2. A homogeneous assay method for detecting the presence or amount of vascular cell adhesion protein 1 (VCAM-1) using only a sandwich assay and alpha-2-macroglobulin (A2M) using only a competitive assay in a sample, the method comprising:

in the sandwich assay, contacting the sample with a first anti-VCAM-1 antibody, which binds to a first epitope of VCAM-1, wherein the first anti-VCAM-1 antibody is labeled with a first donor fluorophore;

contacting the sample with a second anti-VCAM-1 antibody, which binds a second epitope of VCAM-1, wherein the second anti-VCAM-1 antibody is labeled with a first acceptor fluorophore;

in the competitive assay, contacting the sample with an anti-A2M antibody, which binds an epitope to A2M, wherein the anti-A2M antibody is labeled with a second acceptor fluorophore;

contacting the sample with an isolated A2M protein, wherein the isolated A2M protein is labeled with a second donor fluorophore;

incubating the sample for a time sufficient to obtain dual antibody labeled VCAM-1 and antibody labeled A2M; and exciting the sample having dual antibody labeled VCAM-1 and antibody labeled A2M using one or more light sources to detect a single fluorescence emission signal associated with fluorescence resonance energy transfer (FRET) for the first acceptor fluorophore and a single fluorescence emission signal associated with FRET for the second acceptor fluorophore, wherein the first and second acceptor fluorophores are different.

3. The method of claim 1, wherein the first and second donor fluorophores are the same and the sample is excited using one light source.

4. The method of claim 1, wherein the first and second donor fluorophores are different and the sample is excited using two different light sources.

5. The method according to claim 1, wherein the FRET emission signals are time resolved FRET emission signals.

6. The method according to claim 1, wherein the sample is a biological sample.

7. The method according to claim 6, wherein the biological sample is selected from the group consisting of whole blood, urine, a fecal specimen, plasma, and serum.

8. The method according to claim 7, wherein the biological sample is whole blood.

9. The method according to claim 1, wherein the first donor fluorophore is a terbium cryptate.

10. The method according to claim 1, wherein the first acceptor fluorophore or the second acceptor fluorophore is independently selected from the group consisting of fluorescein-like (green zone), Cy5, DY-647, Alexa Fluor 488, Alexa Fluor 546, Alexa Fluor 647, allophycocyanin (APC), and phycoerythrin (PE).

11. The method according to claim 1, wherein the first acceptor fluorophore is Alexa Fluor 488 and the second acceptor fluorophore is Alexa Fluor 546.

12. The method according to claim 1, wherein the first acceptor fluorophore is Alexa Fluor 488 and the second acceptor fluorophore is Alexa Fluor 647.

13. The method according to claim 1, wherein the first acceptor fluorophore is Alexa Fluor 546 and the second acceptor fluorophore is Alexa Fluor 647.

14. The method according to claim 1, further comprising detecting the presence or amount of an additional biomarker.

15. The method according to claim 14, comprising:
contacting the sample with an additional antibody, which binds a first epitope of the additional biomarker, wherein the additional antibody is labeled with a third donor fluorophore;
contacting the sample with a further antibody, which binds a second epitope of the additional biomarker, wherein the further antibody is labeled with a third acceptor fluorophore;
incubating the sample for a time sufficient to obtain dual antibody labeled additional biomarker; and
exciting the sample having dual labeled additional biomarker using a light source to detect two fluorescence emission signals associated with fluorescence resonance energy transfer (FRET),
wherein the first, second, and third acceptor fluorophores are different.

16. The method according to claim 1, wherein the light source provides an excitation wavelength between about 300 nm to about 400 nm.

17. The method according to claim 1, wherein the fluorescence emission signals emit emission wavelengths that are between about 450 nm to 700 nm.

18. The method according to claim 8, wherein the concentration of VCAM-1 in whole blood is about 100 ng/mL to about 1500 ng/mL.

19. The method according to claim 18, wherein the normal concentration of VCAM-1 in whole blood is about 100 ng/mL to about 500 ng/mL.

20. The method according to claim 8, wherein the concentration of A2M in whole blood is about 0.1 mg/mL to about 10 mg/mL.

* * * * *

SEQUENCE LISTING

<160> NUMBER OF SEQ ID NOS: 2

<210> SEQ ID NO 1
<211> LENGTH: 739
<212> TYPE: PRT
<213> ORGANISM: Homo sapiens

<400> SEQUENCE: 1

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
            20                  25                  30

Ser Arg Tyr Leu Ala Gln Ile Gly Asp Ser Val Ser Leu Thr Cys Ser

```
                35                  40                  45
Thr Thr Gly Cys Glu Ser Pro Phe Phe Ser Trp Arg Thr Gln Ile Asp
 50                  55                  60

Ser Pro Leu Asn Gly Lys Val Thr Asn Glu Gly Thr Thr Ser Thr Leu
 65                  70                  75                  80

Thr Met Asn Pro Val Ser Phe Gly Asn Glu His Ser Tyr Leu Cys Thr
                 85                  90                  95

Ala Thr Cys Glu Ser Arg Lys Leu Glu Lys Gly Ile Gln Val Glu Ile
             100                 105                 110

Tyr Ser Phe Pro Lys Asp Pro Glu Ile His Leu Ser Gly Pro Leu Glu
         115                 120                 125

Ala Gly Lys Pro Ile Thr Val Lys Cys Ser Val Ala Asp Val Tyr Pro
     130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
    290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
            340                 345                 350

Ser Pro Leu Ser Gly Lys Val Arg Ser Glu Gly Thr Asn Ser Thr Leu
        355                 360                 365

Thr Leu Ser Pro Val Ser Phe Glu Asn Glu His Ser Tyr Leu Cys Thr
    370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
            420                 425                 430

Leu Asp Arg Leu Glu Ile Glu Leu Leu Lys Gly Glu Thr Ile Leu Glu
        435                 440                 445

Asn Ile Glu Phe Leu Glu Asp Thr Asp Met Lys Ser Leu Glu Asn Lys
    450                 455                 460
```

```
Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
            500                 505                 510

Asp Thr Thr Val Leu Val Ser Pro Ser Ser Ile Leu Glu Glu Gly Ser
            515                 520                 525

Ser Val Asn Met Thr Cys Leu Ser Gln Gly Phe Pro Ala Pro Lys Ile
530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590

Glu Leu Ile Ile Gln Val Thr Pro Lys Asp Ile Lys Leu Thr Ala Phe
            595                 600                 605

Pro Ser Glu Ser Val Lys Glu Gly Asp Thr Val Ile Ile Ser Cys Thr
            610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
                660                 665                 670

Lys Val Gly Ser Gln Leu Arg Ser Leu Thr Leu Asp Val Gln Gly Arg
            675                 680                 685

Glu Asn Asn Lys Asp Tyr Phe Ser Pro Glu Leu Leu Val Leu Tyr Phe
            690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val

<210> SEQ ID NO 2
<211> LENGTH: 1474
<212> TYPE: PRT
<213> ORGANISM: Homo sapiens

<400> SEQUENCE: 2

Met Gly Lys Asn Lys Leu Leu His Pro Ser Leu Val Leu Leu Leu Leu
1               5                   10                  15

Val Leu Leu Pro Thr Asp Ala Ser Val Ser Gly Lys Pro Gln Tyr Met
                20                  25                  30

Val Leu Val Pro Ser Leu Leu His Thr Glu Thr Thr Glu Lys Gly Cys
            35                  40                  45

Val Leu Leu Ser Tyr Leu Asn Glu Thr Val Thr Val Ser Ala Ser Leu
        50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95
```

```
Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
    210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
        275                 280                 285

Lys Phe Ser Gly Gln Leu Asn Ser His Gly Cys Phe Tyr Gln Gln Val
    290                 295                 300

Lys Thr Lys Val Phe Gln Leu Lys Arg Lys Glu Tyr Glu Met Lys Leu
305                 310                 315                 320

His Thr Glu Ala Gln Ile Gln Glu Gly Thr Val Val Glu Leu Thr
                325                 330                 335

Gly Arg Gln Ser Ser Glu Ile Thr Arg Thr Ile Thr Lys Leu Ser Phe
            340                 345                 350

Val Lys Val Asp Ser His Phe Arg Gln Gly Ile Pro Phe Phe Gly Gln
        355                 360                 365

Val Arg Leu Val Asp Gly Lys Gly Val Pro Ile Pro Asn Lys Val Ile
    370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
            420                 425                 430

Gly Tyr Gln Trp Val Ser Glu Glu His Glu Glu Ala His His Thr Ala
        435                 440                 445

Tyr Leu Val Phe Ser Pro Ser Lys Ser Phe Val His Leu Glu Pro Met
    450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
            500                 505                 510
```

```
Leu Leu Val Lys Gln Glu Asp Met Lys Gly His Phe Ser Ile Ser Ile
            515                 520                 525

Pro Val Lys Ser Asp Ile Ala Pro Val Ala Arg Leu Leu Ile Tyr Ala
        530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
            580                 585                 590

Ser Val Cys Ala Leu Arg Ala Val Asp Gln Ser Val Leu Leu Met Lys
        595                 600                 605

Pro Asp Ala Glu Leu Ser Ala Ser Ser Val Tyr Asn Leu Leu Pro Glu
610                 615                 620

Lys Asp Leu Thr Gly Phe Pro Gly Pro Leu Asn Asp Gln Asp Asn Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
            660                 665                 670

Met Gly Leu Lys Ala Phe Thr Asn Ser Lys Ile Arg Lys Pro Lys Met
        675                 680                 685

Cys Pro Gln Leu Gln Gln Tyr Glu Met His Gly Pro Glu Gly Leu Arg
690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
                725                 730                 735

Glu Thr Trp Ile Trp Asp Leu Val Val Asn Ser Ala Gly Val Ala
            740                 745                 750

Glu Val Gly Val Thr Val Pro Asp Thr Ile Thr Glu Trp Lys Ala Gly
        755                 760                 765

Ala Phe Cys Leu Ser Glu Asp Ala Gly Leu Gly Ile Ser Ser Thr Ala
770                 775                 780

Ser Leu Arg Ala Phe Gln Pro Phe Phe Val Glu Leu Thr Met Pro Tyr
785                 790                 795                 800

Ser Val Ile Arg Gly Glu Ala Phe Thr Leu Lys Ala Thr Val Leu Asn
                805                 810                 815

Tyr Leu Pro Lys Cys Ile Arg Val Ser Val Gln Leu Glu Ala Ser Pro
            820                 825                 830

Ala Phe Leu Ala Val Pro Val Glu Lys Glu Gln Ala Pro His Cys Ile
        835                 840                 845

Cys Ala Asn Gly Arg Gln Thr Val Ser Trp Ala Val Thr Pro Lys Ser
850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
                885                 890                 895

Asp Thr Val Ile Lys Pro Leu Leu Val Glu Pro Glu Gly Leu Glu Lys
            900                 905                 910

Glu Thr Thr Phe Asn Ser Leu Leu Cys Pro Ser Gly Gly Glu Val Ser
        915                 920                 925

Glu Glu Leu Ser Leu Lys Leu Pro Pro Asn Val Val Glu Glu Ser Ala
```

```
                930             935             940
Arg Ala Ser Val Ser Val Leu Gly Asp Ile Leu Gly Ser Ala Met Gln
945             950             955             960

Asn Thr Gln Asn Leu Leu Gln Met Pro Tyr Gly Cys Gly Glu Gln Asn
            965             970             975

Met Val Leu Phe Ala Pro Asn Ile Tyr Val Leu Asp Tyr Leu Asn Glu
            980             985             990

Thr Gln Gln Leu Thr Pro Glu Ile Lys Ser Lys Ala Ile Gly Tyr Leu
        995             1000            1005

Asn Thr Gly Tyr Gln Arg Gln Leu Asn Tyr Lys His Tyr Asp Gly
    1010            1015            1020

Ser Tyr Ser Thr Phe Gly Glu Arg Tyr Gly Arg Asn Gln Gly Asn
    1025            1030            1035

Thr Trp Leu Thr Ala Phe Val Leu Lys Thr Phe Ala Gln Ala Arg
    1040            1045            1050

Ala Tyr Ile Phe Ile Asp Glu Ala His Ile Thr Gln Ala Leu Ile
    1055            1060            1065

Trp Leu Ser Gln Arg Gln Lys Asp Asn Gly Cys Phe Arg Ser Ser
    1070            1075            1080

Gly Ser Leu Leu Asn Asn Ala Ile Lys Gly Gly Val Glu Asp Glu
    1085            1090            1095

Val Thr Leu Ser Ala Tyr Ile Thr Ile Ala Leu Leu Glu Ile Pro
    1100            1105            1110

Leu Thr Val Thr His Pro Val Val Arg Asn Ala Leu Phe Cys Leu
    1115            1120            1125

Glu Ser Ala Trp Lys Thr Ala Gln Glu Gly Asp His Gly Ser His
    1130            1135            1140

Val Tyr Thr Lys Ala Leu Leu Ala Tyr Ala Phe Ala Leu Ala Gly
    1145            1150            1155

Asn Gln Asp Lys Arg Lys Glu Val Leu Lys Ser Leu Asn Glu Glu
    1160            1165            1170

Ala Val Lys Lys Asp Asn Ser Val His Trp Glu Arg Pro Gln Lys
    1175            1180            1185

Pro Lys Ala Pro Val Gly His Phe Tyr Glu Pro Gln Ala Pro Ser
    1190            1195            1200

Ala Glu Val Glu Met Thr Ser Tyr Val Leu Leu Ala Tyr Leu Thr
    1205            1210            1215

Ala Gln Pro Ala Pro Thr Ser Glu Asp Leu Thr Ser Ala Thr Asn
    1220            1225            1230

Ile Val Lys Trp Ile Thr Lys Gln Gln Asn Ala Gln Gly Gly Phe
    1235            1240            1245

Ser Ser Thr Gln Asp Thr Val Val Ala Leu His Ala Leu Ser Lys
    1250            1255            1260

Tyr Gly Ala Ala Thr Phe Thr Arg Thr Gly Lys Ala Ala Gln Val
    1265            1270            1275

Thr Ile Gln Ser Ser Gly Thr Phe Ser Ser Lys Phe Gln Val Asp
    1280            1285            1290

Asn Asn Asn Arg Leu Leu Leu Gln Gln Val Ser Leu Pro Glu Leu
    1295            1300            1305

Pro Gly Glu Tyr Ser Met Lys Val Thr Gly Glu Gly Cys Val Tyr
    1310            1315            1320

Leu Gln Thr Ser Leu Lys Tyr Asn Ile Leu Pro Glu Lys Glu Glu
    1325            1330            1335
```

```
Phe Pro Phe Ala Leu Gly Val Gln Thr Leu Pro Gln Thr Cys Asp
    1340            1345            1350

Glu Pro Lys Ala His Thr Ser Phe Gln Ile Ser Leu Ser Val Ser
    1355            1360            1365

Tyr Thr Gly Ser Arg Ser Ala Ser Asn Met Ala Ile Val Asp Val
    1370            1375            1380

Lys Met Val Ser Gly Phe Ile Pro Leu Lys Pro Thr Val Lys Met
    1385            1390            1395

Leu Glu Arg Ser Asn His Val Ser Arg Thr Glu Val Ser Ser Asn
    1400            1405            1410

His Val Leu Ile Tyr Leu Asp Lys Val Ser Asn Gln Thr Leu Ser
    1415            1420            1425

Leu Phe Phe Thr Val Leu Gln Asp Val Pro Val Arg Asp Leu Lys
    1430            1435            1440

Pro Ala Ile Val Lys Val Tyr Asp Tyr Tyr Glu Thr Asp Glu Phe
    1445            1450            1455

Ala Ile Ala Glu Tyr Asn Ala Pro Cys Ser Lys Asp Leu Gly Asn
    1460            1465            1470

Ala
```